United States Patent
Connor et al.

(10) Patent No.: US 12,391,912 B2
(45) Date of Patent: Aug. 19, 2025

(54) SYSTEMS AND METHODS FOR INCREASED PRODUCTION OF RECOMBINANT BIOPOLYMERS VIA GENOME ENGINEERING AND DOWNREGULATION OF BASAL EXPRESSION

(71) Applicant: RENSSELAER POLYTECHNIC INSTITUTE, Troy, NY (US)

(72) Inventors: Alexander Joseph Connor, Slingerlands, NY (US); Mattheos Koffas, Niskayuna, NY (US); Runye Zha, Troy, NY (US); Derek Nelson, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 18/704,718

(22) PCT Filed: Oct. 26, 2022

(86) PCT No.: PCT/US2022/078686
§ 371 (c)(1),
(2) Date: Apr. 25, 2024

(87) PCT Pub. No.: WO2023/076924
PCT Pub. Date: May 4, 2023

(65) Prior Publication Data
US 2024/0327781 A1 Oct. 3, 2024

Related U.S. Application Data

(60) Provisional application No. 63/419,110, filed on Oct. 25, 2022, provisional application No. 63/271,922, filed on Oct. 26, 2021.

(51) Int. Cl.
*C12N 1/20* (2006.01)
*C07K 14/245* (2006.01)
*C12N 15/70* (2006.01)
*C12R 1/19* (2006.01)

(52) U.S. Cl.
CPC ............ *C12N 1/205* (2021.05); *C07K 14/245* (2013.01); *C12N 15/70* (2013.01); *C12R 2001/19* (2021.05)

(58) Field of Classification Search
None
See application file for complete search history.

(56) References Cited

U.S. PATENT DOCUMENTS

| | | |
|---|---|---|
| 5,770,697 A | 6/1998 | Ferrari et al. |
| 6,268,169 B1 | 7/2001 | Fahnestock |
| 6,608,242 B1 | 8/2003 | Yang |
| 6,965,060 B2 | 11/2005 | Yang |
| 7,057,023 B2 | 6/2006 | Islam et al. |
| 7,521,228 B2 | 4/2009 | Lewis et al. |
| 7,723,109 B2 | 5/2010 | Lewis |
| 7,951,908 B2 | 5/2011 | Scheibel et al. |
| 8,372,436 B2 | 2/2013 | Scheibel et al. |
| 8,481,681 B2 | 7/2013 | Sutherland et al. |
| 8,674,077 B2 | 3/2014 | Sutherland et al. |
| 8,729,235 B2 | 5/2014 | Johansson et al. |
| 8,993,844 B1 | 3/2015 | Sylvester et al. |
| 9,475,852 B2 | 10/2016 | Bogush et al. |
| 2006/0248615 A1* | 11/2006 | Scheller ............ C12N 15/8257 435/468 |
| 2010/0197567 A1 | 8/2010 | Maricq et al. |
| 2019/0225933 A1* | 7/2019 | Jayakody ................ C12N 1/20 |

FOREIGN PATENT DOCUMENTS

| | | | |
|---|---|---|---|
| WO | 1999045955 A1 | 9/1999 | |
| WO | WO-9945955 A1 * | 9/1999 | ......... A61K 38/1709 |
| WO | 2008019183 A2 | 2/2008 | |
| WO | 20200198657 A1 | 10/2020 | |

OTHER PUBLICATIONS

Wu et al. Journal of American Chemical Society (Web) Nov. 19, 2018 (Year: 2018).*
Roberts et al. Febs Letters vol. 589, pp. 2477-2486 , 2015. (Year: 2015).*
International Search Report and the Written Opinion of the International Searching Authority, International Application No. PCT/US2022/078686, mailed Feb. 28, 2023.
Wu, X.L., et al., "An Intrinsically Disordered Peptide-Peptide Stapler for Highly Efficient Protein Ligation Both in vivo and in vitro," Journal of the American Chemical Society, pp. 1-12, 2018.

* cited by examiner

*Primary Examiner* — Jana A Hines
*Assistant Examiner* — Khatol S Shahnan Shah
(74) *Attorney, Agent, or Firm* — Barclay Damon LLP; Anthony P. Gangemi

(57) ABSTRACT

Recombinant *E. coli* strains and synthetic protein sequence designs are leveraged for production of disordered polypeptides such as spidroins and elastin-like peptides (ELPs). These disordered polypeptides, the high-titer production of which has proven difficult, include repeating structural motifs from a small selection of amino acid residues, resulting in lack of well-defined tertiary and quaternary structure. The recombinant *E. coli* include expression vectors with genes encoding for the disordered polypeptide product. Expression of these genes is controlled by a promoter that downregulates and substantially inhibits basal expression in the recombinant bacteria. Further, the recombinant bacteria include mutations to one or more stress-response genes from wild-type *E. coli*, such as yggw, yedv, yedw, yedy, spec, speb, uspc, hcha, loip, mltc, envz, ompr, yhgf, or hupb. The recombinant *E. coli* enable production of high titers of disordered protein product while minimizing the toxic effects thereof on the host.

6 Claims, 18 Drawing Sheets
Specification includes a Sequence Listing.

SEQUENCE LISTING

```
Sequence total quantity: 9
SEQ ID NO: 1            moltype = AA  length = 35
FEATURE                 Location/Qualifiers
source                  1..35
                        mol_type = protein
                        organism = synthetic construct
SEQUENCE: 1
GPGQQAAAAA GPGQQGPGQQ GPGQQGPGEQ GPGSG                                    35

SEQ ID NO: 2            moltype = AA  length = 35
FEATURE                 Location/Qualifiers
source                  1..35
                        mol_type = protein
                        organism = synthetic construct
SEQUENCE: 2
GPGQQAAAAA AAAAAGPGQQ GPGQQGPGEQ GPGSG                                    35

SEQ ID NO: 3            moltype = AA  length = 105
FEATURE                 Location/Qualifiers
source                  1..105
                        mol_type = protein
                        organism = synthetic construct
SEQUENCE: 3
VPGAGVPGAG VPGAGVPGAG VPGYGVPGAG VPGAGVPGAG VPGAGVPGYG VPGAGVPGAG         60
VPGAGVPGAG VPGYGVPGAG VPGAGVPGAG VPGAGVPGYG GRGDS                        105

SEQ ID NO: 4            moltype = AA  length = 174
FEATURE                 Location/Qualifiers
source                  1..174
                        mol_type = protein
                        organism = synthetic construct
SEQUENCE: 4
MGHHHHHHHH HHSSGHIDDD DKHMLEHMPG GPGQQAAAAA GPGQQGPGQQ GPGQQGPGEQ         60
GPGSGGPGQQ AAAAAGPGQQ GPGQQGPGQQ GPGEQGPGSG GPGQQAAAAA GPGQQGPGQQ        120
GPGQQGPGEQ GPGSGGPGQQ AAAAAGPGQQ GPGQQGPGQQ GPGEQGPGSG TSGS              174

SEQ ID NO: 5            moltype = AA  length = 594
FEATURE                 Location/Qualifiers
source                  1..594
                        mol_type = protein
                        organism = synthetic construct
SEQUENCE: 5
MGHHHHHHHH HHSSGHIDDD DKHMLEHMPG GPGQQAAAAA GPGQQGPGQQ GPGQQGPGEQ         60
GPGSGGPGQQ AAAAAGPGQQ GPGQQGPGQQ GPGEQGPGSG GPGQQAAAAA GPGQQGPGQQ        120
GPGQQGPGEQ GPGSGGPGQQ AAAAAGPGQQ GPGQQGPGQQ GPGEQGPGSG GPGQQAAAAA        180
GPGQQGPGQQ GPGQQGPGEQ GPGSGGPGQQ AAAAAGPGQQ GPGQQGPGQQ GPGEQGPGSG        240
GPGQQAAAAA GPGQQGPGQQ GPGQQGPGEQ GPGSGGPGQQ AAAAAGPGQQ GPGQQGPGQQ        300
GPGEQGPGSG GPGQQAAAAA GPGQQGPGQQ GPGQQGPGEQ GPGSGGPGQQ AAAAAGPGQQ        360
GPGQQGPGQQ GPGEQGPGSG GPGQQAAAAA GPGQQGPGQQ GPGQQGPGEQ GPGSGGPGQQ        420
AAAAAGPGQQ GPGQQGPGQQ GPGEQGPGSG GPGQQAAAAA GPGQQGPGQQ GPGQQGPGEQ        480
GPGSGGPGQQ AAAAAGPGQQ GPGQQGPGQQ GPGEQGPGSG GPGQQAAAAA GPGQQGPGQQ        540
GPGQQGPGEQ GPGSGGPGQQ AAAAAGPGQQ GPGQQGPGQQ GPGEQGPGSG TSGS              594

SEQ ID NO: 6            moltype = AA  length = 174
FEATURE                 Location/Qualifiers
source                  1..174
```

```
                         mol_type = protein
                         organism = synthetic construct
SEQUENCE: 6
MGHHHHHHHH HHSSGHIDDD DKHMLEHMPG GPGQQAAAAA AAAAAGPGQQ GPGQQGPGEQ    60
GPGSGGPGQQ AAAAAAAAAA GPGQQGPGQQ GPGEQGPGSG GPGQQAAAAA AAAAAGPGQQ   120
GPGQQGPGEQ GPGSGGPGQQ AAAAAAAAAA GPGQQGPGQQ GPGEQGPGSG TSGS         174

SEQ ID NO: 7             moltype = AA  length = 594
FEATURE                  Location/Qualifiers
source                   1..594
                         mol_type = protein
                         organism = synthetic construct
SEQUENCE: 7
MGHHHHHHHH HHSSGHIDDD DKHMLEHMPG GPGQQAAAAA AAAAAGPGQQ GPGQQGPGEQ    60
GPGSGGPGQQ AAAAAAAAAA GPGQQGPGQQ GPGEQGPGSG GPGQQAAAAA AAAAAGPGQQ   120
GPGQQGPGEQ GPGSGGPGQQ AAAAAAAAAA GPGQQGPGQQ GPGEQGPGSG GPGQQAAAAA   180
AAAAAGPGQQ GPGQQGPGEQ GPGSGGPGQQ AAAAAAAAAA GPGQQGPGQQ GPGEQGPGSG   240
GPGQQAAAAA AAAAAGPGQQ GPGQQGPGEQ GPGSGGPGQQ AAAAAAAAAA GPGQQGPGQQ   300
GPGEQGPGSG GPGQQAAAAA AAAAAGPGQQ GPGQQGPGEQ GPGSGGPGQQ AAAAAAAAAA   360
GPGQQGPGQQ GPGEQGPGSG GPGQQAAAAA AAAAAGPGQQ GPGQQGPGEQ GPGSGGPGQQ   420
AAAAAAAAAA GPGQQGPGQQ GPGEQGPGSG GPGQQAAAAA AAAAAGPGQQ GPGQQGPGEQ   480
GPGSGGPGQQ AAAAAAAAAA GPGQQGPGQQ GPGEQGPGSG GPGQQAAAAA AAAAAGPGQQ   540
GPGQQGPGEQ GPGSGGPGQQ AAAAAAAAAA GPGQQGPGQQ GPGEQGPGSG TSGS         594

SEQ ID NO: 8             moltype = AA  length = 188
FEATURE                  Location/Qualifiers
source                   1..188
                         mol_type = protein
                         organism = synthetic construct
SEQUENCE: 8
MGHHHHHHHH HHSSGHIDDD DKHMLEHMVP GAGVPGAGVP GAGVPGAGVP GYGVPGAGVP    60
GAGVPGAGVP GAGVPGYGGR GDSVPGAGVP GAGVPGAGVP GAGVPGYGVP GAGVPGAGVP   120
GAGVPGAGVP GYGGRGDSVP GAGVPGAGVP GAGVPGAGVP GYGVPGAGVP GAGVPGAGVP   180
GAGVPGYG                                                           188

SEQ ID NO: 9             moltype = AA  length = 464
FEATURE                  Location/Qualifiers
source                   1..464
                         mol_type = protein
                         organism = synthetic construct
SEQUENCE: 9
MGHHHHHHHH HHSSGHIDDD DKHMLEHMQA NTPWSSKANA DAFINSFISA ASNTGSFSQD    60
QMEDMSLIGN TLMAAMDNMG GRITPSKLQA LDMAFASSVA EIAASEGGDL GVTTNAIADA   120
LTSAFYQTTG VVNSRFISEI RSLIGMFAQA SANDVYASAG SSGGGGYGAS SASAASASAA   180
APSGVAYQAP AQAQISFTLR GQQPVSGPGQ QAAAAAAAAA AGPGQQGPGQ QGPGEQGPGS   240
GGPGQQAAAA AAAAAGPGQ QGPGQQGPGE QGPGSGGPGQ QAAAAAAAAA AGPGQQGPGQ    300
QGPGEQGPGS GGPGQQAAAA AAAAAGPGQ QGPGQQGPGE QGPGSGSGPG QIYYGPQSVA    360
APAAAAASAL AAPATSARIS SHASALLSNG PTNPASISNV ISNAVSQISS SNPGASACDV   420
LVQALLELVT ALLTIIGSSN IGSVNYDSSG QYAQWTQSVQ NAFA                    464
```

SYSTEMS AND METHODS FOR INCREASED PRODUCTION OF RECOMBINANT BIOPOLYMERS VIA GENOME ENGINEERING AND DOWNREGULATION OF BASAL EXPRESSION

CROSS REFERENCE TO RELATED APPLICATION(S)

This application is a national stage filing of International Patent Application No. PCT/US2022/078686, filed Oct. 26, 2022, which claims the benefit of U.S. Provisional Application Nos. 63/271,922, filed Oct. 26, 2021, and 63/419,110, filed Oct. 25, 2022, which are incorporated by reference as if disclosed herein in their entireties.

STATEMENT REGARDING FEDERALLY SPONSORED RESEARCH AND DEVELOPMENT

This invention was made with U.S. Government support under Grant Number 2036768 awarded by the National Science Foundation. The United States Government has certain rights in the invention.

INCORPORATION OF SEQUENCE LISTING

The contents of the text file named "Sequences_final.xml", which was created on Oct. 26, 2022 and is 10.9 KB is size, are hereby incorporated by reference in their entireties.

BACKGROUND

Spider silk proteins (spidroins) and elastin-like peptides (ELPs) are desirable for a broad range of applications due to their unmatched combination of properties. However, harvesting spidroins or ELPs from nature is inefficient and impractical, and not useful in generating engineered varieties of these structural biopolymers.

Silk is a protein-based material with extraordinary properties. Produced by many orders of arachnids and insects, such as Lepidoptera, Hymenoptera, Diptera, Neuroptera, and Araneae, silk functions as a structural fiber spun on demand for applications ranging from prey capture to egg encasement. To date, some of the most commonly studied silks have been derived from the cocoons of Bombyx mori silkworms, which have been domestically cultured for thousands of years for the production of silk textiles. More recently, silk threads from several orb-weaver spider species, including Araneus diadematus and Nephila clavipes, have been studied extensively.

Spidroins are of intense interest to engineers and researchers due to their high value material properties and utility in diverse applications. With only a fraction of the density of steel, dragline silk can surpass even high-performance materials such as carbon fiber and Kevlar in toughness. This toughness results from a relatively high ultimate tensile strength combined with excellent extensibility, allowing dragline silk fibers to absorb the energy of high impact collisions from large prey. In comparison to man-made polymers, the combination of strength, toughness, and stiffness exhibited by silk is unmatched. In addition, silk is biodegradable, thermally stable up to 285° C., and lightweight.

Orb-weaving spiders produce up to seven different types of silk, with dragline (major ampullate) silk serving as a safety line and framework of the web. Dragline silk fibers are five times stronger by weight than steel and three times tougher than the top-quality man-made fiber Kevlar. Additionally, silk is biodegradable and biocompatible, and silk proteins can be processed into numerous morphologies including coatings, hydrogels, and tissue scaffolds. As such, the applications of silk proteins range from next-generation body armor to optofluidic devices and even coatings for food preservation. While silk protein from the Bombyx mori silkworm is farmed at scale for the textiles industry, dragline silk cannot be readily obtained through farming, as spiders are territorial and cannibalistic. Thus, researchers have used recombinant production to obtain proteins that mimic or directly copy the sequences of natural dragline spidroins. Recombinant production currently represents the most promising method for producing dragline spidroins at scale while also presenting the ability to rationally design protein sequences with targeted properties.

The unique properties of dragline spidroins arise from specific peptide motifs, chemical interactions, and hierarchical organization that are highly conserved among orb-weaving spiders. Natural dragline fibers are composed of two proteins, Major Ampullate Spidroin 1 (MaSp1) and Major Ampullate Spidroin 2 (MaSp2) in a ratio of approximately three MaSp1 for every two MaSp2. Major ampullate spidroins are generally quite large at 250-350 kDa and take the form of a segmented copolymer with small non-repetitive N and C-terminal domains that flank a large repetitive core domain. The repetitive domain of dragline spidroins represents approximately 90% of the total protein, with repeating units that are typically 33-45 amino acids long. The repeat unit of MaSp1 is characterized by a tandem alanine repeat ($A_n$, where n ~6-9) adjacent to a glycine-rich region that contains GGX motifs, where X often represents tyrosine (Y), glutamine (Q), or leucine (L). The repeat unit of MaSp2 also contains tandem alanine repeats, but its glycine-rich region is high in proline (P) and contains GPGXX and GGX motifs, where X often represents Q, Y, L, G, or serine (S). In both MaSp1 and MaSp2, the tandem alanine segments assemble into beta-sheet nanocrystals, and the glycine-rich regions form an amorphous matrix during fiber spinning. The interplay between these crystalline and amorphous domains endows spider silk with many of its unique properties, including a combination of high tensile strength and toughness.

Both natural and synthetic spidroins have been produced recombinantly. Natural spidroins are typically created from cDNA taken directly from the species of interest. Recombinant silk has been produced in a diverse set of host organisms, including bacteria, yeast, mammalian cells, insect cells, transgenic plants, and transgenic animals. Common practice in the field to create synthetic spider silk genes is to combine spidroin amino acid motifs (GGX, $(A)_n$, etc.) in ways that mimic the repetitive core of a natural dragline sequence. This is due to the difficulty in obtaining exact copies of full-length dragline spidroin genes by PCR, as they are long, repetitive, and have a high GC content. In vivo and in vitro fiber formation for spider silk proteins typically involves the multiscale aggregation of individual silk proteins. The hydrophobic, and alanine rich, regions of several individual proteins aggregate to form nanofibrils and nanocrystals. These nanostructures then continue to interact and aggregate to form larger micrometer-scale fibrils, which interact and tangle to form the mature fibers.

Recombinantly produced dragline spidroins generally have anywhere from 2-196 repeats of a relatively short "monomer" segment (typically around 35 amino acids) and may or may not include non-repetitive terminal domains. Most efforts to produce recombinant spidroins have suffered from low titers, preventing the production and utilization of artificial spider silk at a commercial scale. Additionally, expressing recombinant spidroins in bacteria is often plagued by a high degree of plasmid instability, inclusion body formation, low solubility of the spidroin constructs, and transcriptional and translational errors. These issues, particularly the low titers, correlate with recombinant spidroin size, which further limits the production of useful materials, as increasing spidroin size has been shown to increase the mechanical properties of resultant fibers. However, high titers of recombinant spidroins are possible. Using an E. coli host system, titers of 3.6 g/L for 200 kDa dragline spidroin have been achieved in a bioreactor kept at 16° C. A secondary plasmid was also employed to upregulate glycyl-tRNA supply. Furthermore, a titer of 14.5 g/L has been achieved for a small recombinant spidroin using an E. coli host system in a bioreactor. This 33 kDa recombinant spidroin only contained two monomer repeats in its primary sequence, but it could be spun into fibers that exhibited mechanical properties similar to much larger recombinant spidroins.

Elastin is a polymeric extracellular matrix protein including cross-linked tropoelastin monomers that helps to provide elastic properties to tissues such as arteries, ligaments, and lungs. Tropoelastin includes mostly non-polar amino acids arranged in alternating hydrophobic and hydrophilic domains. Within the hydrophobic domains are repeating sequence motifs, which confer elasticity to the protein and contribute to cell signaling. The hydrophilic domains include mainly lysine-rich stretches involved in cross-linking. The structural stability, elastic resilience, and bioactivity of tropoelastin, combined with its capacity for self-assembly, make this protein a highly desirable candidate for the fabrication of biomaterials. Indeed, materials derived from tropoelastin have been implicated for extensive use in tissue engineering and drug delivery. Importantly, these constructs show promise for use in drug delivery settings in which viable alternative vectors may not exist, including biologic therapeutics, radionuclides, and small molecule drugs targeted to specific anatomical sites for the treatment of diseases including cancer, type 2 diabetes, osteoarthritis, and neuroinflammation. Unfortunately, elastin extracted from animal tissue is heterogeneous in mass, sequence and structural topology, and materials derived from these products form structures that exhibit inconsistent and heterogeneous properties. Moreover, animal-sourced elastins may also include pathogens, immunogenic protein sequences, or harsh chemical residues.

Researchers have looked to capitalize on the biomedical potential of elastin by producing recombinant ELPs that are homogenous in structure, properties, and safety. Recombinant ELPs share several similarities with dragline spidroins, including a polymeric structure, a high glycine and proline content, and an ability to self-assemble when triggered by external stimuli. Recombinant ELPs are typically composed of repeated Val-Pro-Gly-X-Gly units derived from the hydrophobic domain of tropoelastin and where X represents a guest residue that can be any amino acid except proline. An advantage of recombinant ELPs includes the ability to customize the construct to include motifs such as RGD integrin binding domains or tyrosine residues for targeted applications, e.g., drug delivery to only a specific tissue.

Notwithstanding, the recombinant production of silk proteins and ELPs is expensive at scale, and the recombinant production of these biopolymers is currently inhibited by this high cost of production that stems from low titers in microbial systems and high purification costs.

SUMMARY

Aspects of the present disclosure are directed to a recombinant bacteria for producing polypeptides. In some embodiments, the recombinant bacterial includes an E. coli strain. In some embodiments, the E. coli strain includes one or more exogenous nucleotide sequences encoding a disordered polypeptide and at least one promoter regulating the expression of the one or more exogenous nucleotide sequences. In some embodiments, basal expression of the one or more exogenous nucleotide sequences in an about 0.6 to about 0.8 OD600 culture of the E. coli strain for about 4 hours of incubation produces less than about 7 mg/L disordered polypeptide in the culture. In some embodiments, basal expression of the one or more exogenous nucleotide sequences is inhibited. In some embodiments, the E. coli strain includes a SoluBL21 genome and a pLysS plasmid.

In some embodiments, the E. coli strain includes one or more mutations to stress-response genes from wild-type E. coli B. In some embodiments, the E. coli strain includes one or more mutations in at least one of the following genes: yggw, yedv, yedw, yedy, spec, speb, uspc, hcha, loip, mltc, envz, ompr, yhgf, and hupb.

In some embodiments, the disordered polypeptide includes between about 30% and about 40% glycine residues and between about 10% and about 20% proline residues. In some embodiments, the disordered polypeptide includes between about 5% and about 30% beta sheets, between about 25% and about 70% alpha helices, between 0% and about 50% random coils, and between about 5% and about 45% beta-turns. In some embodiments, the disordered polypeptide includes recombinant spidroins, elastin-like peptides (ELPs), or combinations thereof. In some embodiments, the disordered polypeptide includes a primary sequence including GPGQQ AAAAA GPGQQ GPGQQ GPGQQ GPGEQ GPGSG (SEQ. ID NO.: 1) or GPGQQ AAAAA AAAAA GPGQQ GPGQQ GPGEQ GPGSG (SEQ. ID NO.: 2). In some embodiments, the disordered polypeptide includes a primary sequence including (VP-GAGVPGAGVPGAGVPGAGVPGYGVPGAGVP-GAGVPGAGVPGAGVPGYG)2 GRGDS (SEQ. ID NO.: 3). In some embodiments, the disordered polypeptide includes a 2, 4, 8, 16, 32, or 64mer of the primary sequence.

Aspects of the present disclosure are directed to a method of producing one or more exogenous polypeptides. In some embodiments, the method includes preparing an expression vector. In some embodiments, the expression vector includes one or more exogenous nucleotide sequences encoding a disordered polypeptide and at least one promoter regulating the expression of the one or more exogenous nucleotide sequences.

In some embodiments, the method includes inserting the expression vector into an E. coli strain. In some embodiments, basal expression of the one or more exogenous nucleotide sequences in the E. coli strain after 4 hours incubation of an about 0.6 to about 0.8 OD600 culture of the E. coli strain is less than about 7 mg/L disordered polypeptide in the culture. In some embodiments, the method includes inducing expression of the expression vector.

In some embodiments, preparing the expression vector includes preparing a plasmid vector including one or more gene fragments of the disordered polypeptides, the disordered polypeptides including spidroins, ELPs, or combinations thereof, and duplicating the lengths of the one or more gene fragments and inserting them into an expression vector. In some embodiments, the method includes inserting a pLysS plasmid into SoluBL21 E. coli to form the E. coli strain.

Aspects of the present disclosure are directed to a method of producing an exogenous polypeptide product. In some embodiments, the method includes preparing a recombinant E. coli strain, inducing expression of the one or more exogenous nucleotide sequences via application of one or more inducing agents, and isolating a disordered polypeptide from the E. coli strain as a polypeptide product. In some embodiments, the recombinant E. coli strain includes an expression vector including one or more exogenous nucleotide sequences encoding a disordered polypeptide, at least one promoter regulating the expression of the one or more exogenous nucleotide sequences, and one or more mutations in at least one of the following genes: yggw, yedv, yedw, yedy, spec, speb, uspc, hcha, loip, mltc, envz, ompr, yhgf, and hupb. In some embodiments, basal expression of the one or more exogenous nucleotide sequences in the E. coli strain after 4 hours incubation of an about 0.6 to about 0.8 OD600 culture of the E. coli strain is less than about 7 mg/L disordered polypeptide in the culture.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1A:
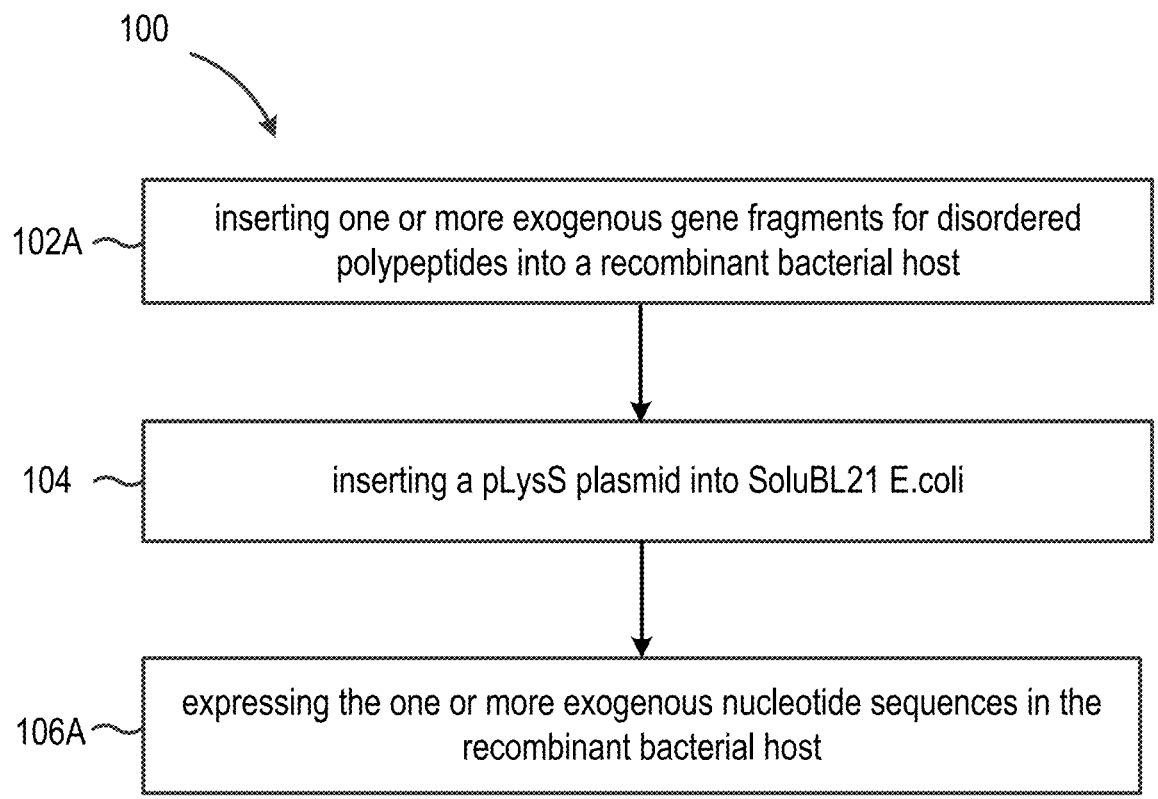
FIG. 1A is a chart of a method of producing one or more exogenous polypeptides according to some embodiments of the present disclosure.

Some embodiments of the present disclosure are directed to a recombinant bacteria for producing polypeptides. In some embodiments, the recombinant bacteria is produced by making one or more genetic modifications to a natural or engineered strain of bacteria. In some embodiments, the recombinant bacteria is produced by making one or more genetic modifications to a strain of E. coli, i.e., is a modified E. coli strain. In some embodiments, the recombinant bacteria is a modified E. coli B strain. In some embodiments, the recombinant bacteria is a modified E. coli SoluBL21 strain. As will be discussed in greater detail below, the recombinant bacteria includes one or more exogenous genes. In some embodiments, the one or more exogenous genes are inserted into the endogenous genetic material of the recombinant bacteria. In some embodiments, the recombinant bacteria includes one or more exogenous plasmids. In some embodiments, the one or more exogenous genes are included in one of the exogenous plasmids. In some embodiments, one or more of the exogenous plasmids is an expression vector. The expression vector is any suitable vector compatible with the recombinant bacterial host and capable of facilitating expression of the one or more exogenous genes included therein. In some embodiments, the expression vector is pET-19b.

As discussed above, the recombinant bacteria includes one or more exogenous nucleotide sequences. In some embodiments, the recombinant bacteria produce at least one exogenous polypeptide via expression of the one or more exogenous nucleotide sequences. In some embodiments, the recombinant bacteria produce two or more exogenous polypeptides. In some embodiments, the recombinant bacteria produce two or more exogenous polypeptides simultaneously. In some embodiments, the exogenous polypeptides include wild-type polypeptides, recombinant polypeptides, or combination thereof.

In some embodiments, the one or more exogenous nucleotides encode a disordered polypeptide. As used herein, the term "disordered polypeptide" is used to refer to a polypeptide with repeating structural motifs made up of a small selection of amino acid residues, resulting in lack of well-defined tertiary and quaternary structure in the polypeptide. In some embodiments, the disordered polypeptide includes between about 20% and about 50% glycine residues. In some embodiments, the disordered polypeptide includes between about 25% and about 45% glycine residues. In some embodiments, the disordered polypeptide includes between about 30% and about 40% glycine residues. In some embodiments, the disordered polypeptide includes between about 5% and about 25% proline residues. In some embodiments, the disordered polypeptide includes between about 10% and about 20% proline residues. In some embodiments, the disordered polypeptide includes more than about 15% glutamine residues. In some embodiments, the disordered polypeptide includes more than about 20% glutamine residues. In some embodiments, the disordered polypeptide includes more than about 10% valine residues. In some embodiments, the disordered polypeptide includes more than about 15% valine residues. In some embodiments, the disordered polypeptide includes above about 0% and below about 5% tyrosine residues. Structurally, in some embodiments, the disordered polypeptide includes above about 0% and below about 35% beta sheets. In some embodiments, the disordered polypeptide includes between about 5% and about 30% beta sheets. In some embodiments, the disordered polypeptide includes between about 5% and about 20% beta sheets. In some embodiments, the disordered polypeptide includes between about 15% and about 30% beta sheets. In some embodiments, the disordered polypeptide includes between about 20% and about 75% alpha helices. In some embodiments, the disordered polypeptide includes between about 25% and about 70% alpha helices. In some embodiments, the disordered polypeptide includes between about 25% and about 50% alpha helices. In some embodiments, the disordered polypeptide includes between about 50% and about 55% alpha helices. In some embodiments, the disordered polypeptide includes between about 45% and about 70% alpha helices. In some embodiments, the disordered polypeptide includes between 0% and about 55% random coils. In some embodiments, the disordered polypeptide includes between 0% and about 50% random coils. In some embodiments, the disordered polypeptide includes between 0% and about 5% random coils. In some embodiments, the disordered polypeptide includes between 25% and about 50% random coils. In some embodiments, the disordered polypeptide includes above about 0% and below about 50% beta-turns. In some embodiments, the disordered polypeptide includes between about 5% and about 45% beta-turns. In some embodiments, the disordered polypeptide includes between about 10% and about 45% beta-turns. In some embodiments, the disordered polypeptide includes between about 20% and about 30% beta-turns. In some embodiments, the disordered polypeptide includes recombinant spidroins, elastin-like peptides (ELPs), or combinations thereof.

In some embodiments, the disordered polypeptide includes a primary sequence including GPGQQ AAAAA GPGQQ GPGQQ GPGQQ GPGEQ GPGSG (SEQ. ID NO.: 1). In some embodiments, the disordered polypeptide includes a primary sequence including GPGQQ AAAAA AAAAA GPGQQ GPGQQ GPGEQ GPGSG (SEQ ID. NO.: 2). In some embodiments, the disordered polypeptide includes ELP constructs combining one or more native elastin motifs of VPGAG with specific placement of tyrosine and GRGDS domains for targeted neurological drug delivery. In some embodiments, the disordered polypeptide includes a primary sequence including: (VPGAGVP-GAGVPGAGVPGAGVPGYGVPGAGVPGAGVP-GAGVPGAGVPGYG)2 GRGDS (SEQ. ID NO.: 3). In some embodiments, the disordered polypeptide is based on two or more distinct and purposefully designed monomers. In some embodiments, the disordered polypeptide is based on two or more distinct and purposefully designed monomers which are duplicated one or more times. In some embodiments, the disordered polypeptide includes a 2, 4, 8, 16, 32, or 64mer of the primary sequence.

In some embodiments, the recombinant bacteria includes one or more mutations to stress-response genes from wild-type *E. coli* B. In some embodiments, the recombinant bacteria includes one or more mutations to one or more of the following stress-response genes: coproporphyrinogen-III oxidase-like protein "yggw", sensory kinase "yedv," transcriptional regulatory protein "yedw," reductase catalytic subunit "yedy," ornithine decarboxylase "spec," *streptococcus* pyrogenic exotoxin B "speb," universal stress protein C "uspc," protein and nucleotide deglycase "hcha," metalloprotease "loip," membrane-bound lytic murein transglycosylase C "mltc," sensor histidine kinase "envz," DNA-binding dual transcriptional regulator "ompr," RNA-binding protein "yhgf," and DNA-binding protein HU-β "hupb." In some embodiments, the one or more mutations includes a base substitution, deletion, insertion, or combinations thereof. Representative mutations consistent with the embodiments of the present disclosure are provided below at Table 1:

TABLE 1

Genetic Mutations in Stress-Response Genes of Recombinant Bacteria consistent with some embodiments of the present disclosure.

| Gene | Mutations |
| --- | --- |
| yggw | Gln60Lys |
|  | Thr91Ala |
|  | Asn150Lys |
|  | Ala305Thr |
|  | Ser334Stop |
|  | Glu336Asp |
| yedv | Gln227His |
|  | Asp99Gly |
|  | Gly86Ser |
| yedw | Gln137His |
| yedy | Ala34Thr |
|  | Pro63Ala |
| spec | Met702Val |
|  | Glu631Asp |
|  | Ala565Val |
|  | Asn496Asp |
|  | Ala418Glu |
|  | Phe275Tyr |
|  | Ile146Val |
|  | Thr18Ser |
| speb | Ser33Ala |
| uspc | Gln62His |
| hcha | Asn164Thr |
| loip | Ala47Thr |
| mltc | Gln164Lys |
| envz | Leu41Pro |
| ompr | Asp183Tyr |
|  | Asn6Lys |
| yhgf | Asp147Tyr |
|  | Val723Glu |
| hupb | Residues Ala57-Thr59 deleted |

In some embodiments, the recombinant bacteria includes at least one promoter regulating the expression of the one or more exogenous nucleotide sequences. In some embodiments, the promoter is any suitable promoter compatible with the recombinant bacteria and capable of being activated in the presence of one or more inducing agents. In some embodiments, the promoter is at least substantially deactivated in the absence of the inducing agent. In some embodiments, the recombinant bacteria has little to no expression of the one or more exogenous nucleotide sequences in the absence of inducing agent, i.e., basal expression of the one or more exogenous nucleotide sequences is low or inhibited. As will be discussed in greater detail below, controlled expression of exogenous polypeptides can be disrupted by so called "leaky" promoters, where a baseline level of polypeptide expression occurs even in the absence of the inducing agent. In some embodiments of the present disclosure, the promoters of the one or more exogenous nucleotide sequences are sufficiently strong and/or downregulated so that such basal expression is limited or inhibited altogether in the absence of inducing agent. In some embodiments, basal expression of the one or more exogenous nucleotide sequences in an about 0.6 to about 0.8 OD600 culture of the recombinant bacteria for about 4 hours of incubation produces less than about 70 mg/L, produces less than about 60 mg/L, produces less than about 50 mg/L, produces less than about 40 mg/L, produces less than about 30 mg/L, produces less than about 20 mg/L, less than about 10 mg/L, less than about 9 mg/L, less than about 8 mg/L, or less than about 7 mg/L disordered polypeptide in the culture. In some embodiments, basal expression of the one or more exogenous nucleotide sequences in a culture of the recombinant bacteria at about 3 hours of incubation post-inoculation produces less than about 7 mg/L. In these embodiments, the term "incubation" is used to refer to bacterial culture performed under conditions suitable to foster bacterial growth, e.g., at about 37° C. for the modified E. coli identified in the exemplary embodiments below. In some embodiments, basal expression of the one or more exogenous nucleotide sequences is inhibited. In some embodiments, the recombinant bacteria includes a SoluBL21 genome. In some embodiments, the recombinant bacteria includes a pLysS plasmid.

Figure 1B:
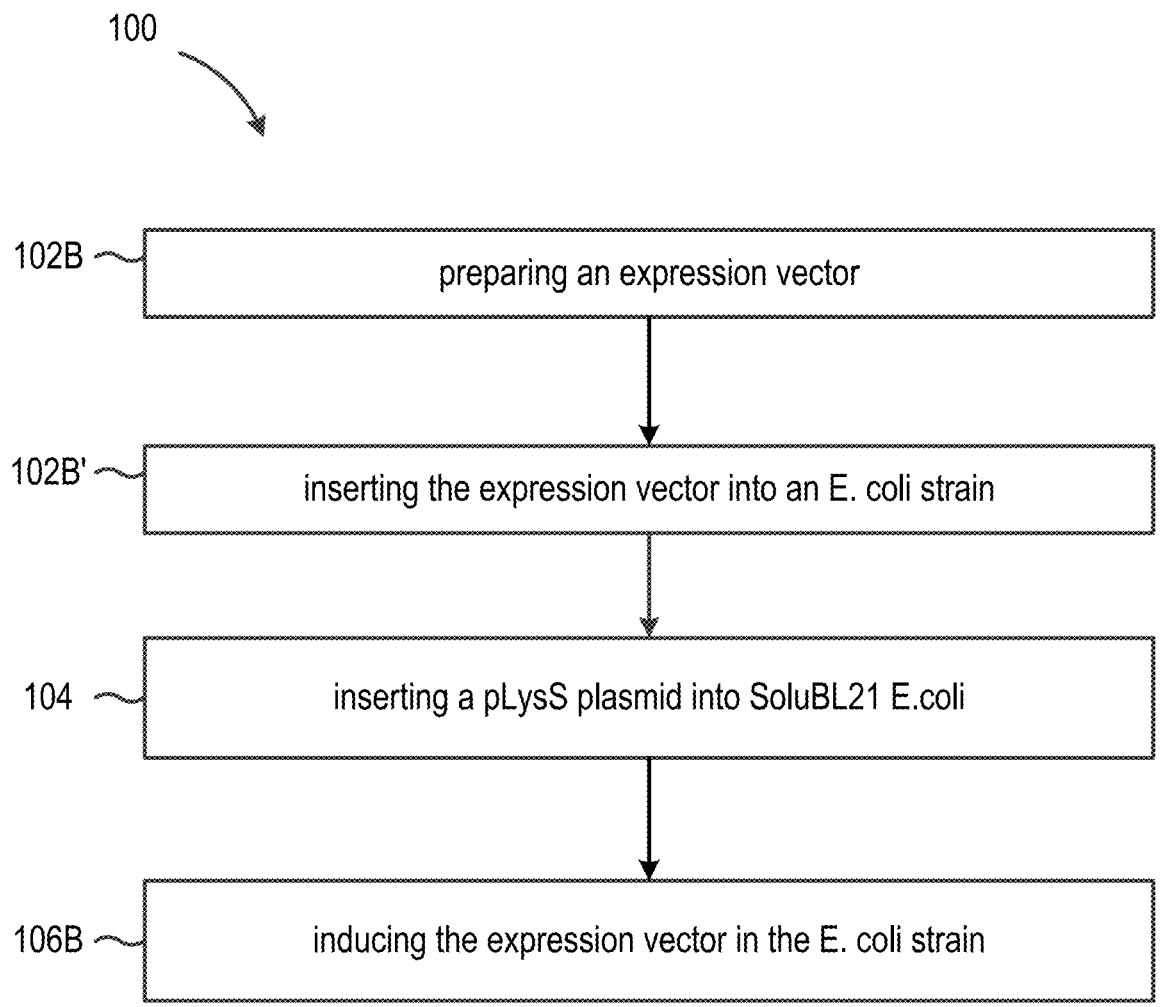
FIG. 1B is a chart of a method of producing one or more exogenous polypeptides according to some embodiments of the present disclosure.

Referring now to FIGS. 1A-1B, some embodiments of the present disclosure are directed to a method 100 of producing one or more exogenous polypeptides. As discussed above, in some embodiments, the disordered polypeptide includes between about 20% and about 50% glycine residues. In some embodiments, the disordered polypeptide includes between about 25% and about 45% glycine residues. In some embodiments, the disordered polypeptide includes between about 30% and about 40% glycine residues. In some embodiments, the disordered polypeptide includes between about 5% and about 25% proline residues. In some embodiments, the disordered polypeptide includes between about 10% and about 20% proline residues. In some embodiments, the disordered polypeptide includes more than about 15% glutamine residues. In some embodiments, the disordered polypeptide includes more than about 20% glutamine residues. In some embodiments, the disordered polypeptide includes more than about 10% valine residues. In some embodiments, the disordered polypeptide includes more than about 15% valine residues. In some embodiments, the disordered polypeptide includes above about 0% and below about 5% tyrosine residues. Structurally, in some embodiments, the disordered polypeptide includes above about 0% and below about 35% beta sheets. In some embodiments, the disordered polypeptide includes between about 5% and about 30% beta sheets. In some embodiments, the disordered polypeptide includes between about 5% and about 20% beta sheets. In some embodiments, the disordered polypeptide includes between about 15% and about 30% beta sheets. In some embodiments, the disordered polypeptide includes between about 20% and about 75% alpha helices. In some embodiments, the disordered polypeptide includes between about 25% and about 70% alpha helices. In some embodiments, the disordered polypeptide includes between about 25% and about 50% alpha helices. In some embodiments, the disordered polypeptide includes between about 50% and about 55% alpha helices. In some embodiments, the disordered polypeptide includes between about 45% and about 70% alpha helices. In some embodiments, the disordered polypeptide includes between 0% and about 55% random coils. In some embodiments, the disordered polypeptide includes between 0% and about 50% random coils. In some embodiments, the disordered polypeptide includes between 0% and about 5% random coils. In some embodiments, the disordered polypeptide includes between 25% and about 50% random coils. In some embodiments, the disordered polypeptide includes above about 0% and below about 50% beta-turns. In some embodiments, the disordered polypeptide includes between about 5% and about 45% beta-turns. In some embodiments, the disordered polypeptide includes between about 10% and about 45% beta-turns. In some embodiments, the disordered polypeptide includes between about 20% and about 30% beta-turns. In some embodiments, the exogenous polypeptides retain a similar primary sequence design and/or function to the analogous wild-type protein. In some embodiments, the disordered polypeptide includes recombinant spidroins, ELPs, or combinations thereof.

In some embodiments, the disordered polypeptide includes a primary sequence including GPGQQ AAAAA GPGQQ GPGQQ GPGQQ GPGEQ GPGSG (SEQ. ID NO.: 1). In some embodiments, the disordered polypeptide includes a primary sequence including GPGQQ AAAAA AAAAA GPGQQ GPGQQ GPGEQ GPGSG (SEQ. ID NO.: 2). In some embodiments, the disordered polypeptide includes ELP constructs combining one or more native elastin motifs of VPGAG with specific placement of tyrosine and GRGDS domains for targeted neurological drug delivery. In some embodiments, the disordered polypeptide includes a primary sequence including: (VPGAGVP-GAGVPGAGVPGAGVPGYGVPGAGVPGAGVP-GAGVPGAGVPGYG)2 GRGDS (SEQ. ID NO.: 3). In some embodiments, the disordered polypeptide is based on two or more distinct and purposefully designed monomers. In some embodiments, the disordered polypeptide is based on two or more distinct and purposefully designed monomers which are duplicated one or more times. In some embodiments, the disordered polypeptide includes a 2, 4, 8, 16, 32, or 64mer of the primary sequence.

At 102A, one or more exogenous gene fragments for the disordered polypeptides are inserted into a recombinant bacterial host. As discussed above, in some embodiments, the recombinant bacterial host is a modified E. coli strain. Referring specifically to FIG. 1B, in an exemplary embodiment of step 102A, an expression vector is prepared at step 102B. As discussed above, the expression vector can be any suitable vector compatible with the recombinant bacterial host and capable of facilitating expression of the one or more exogenous genes included in the vector. In some embodiments, the expression vector is pET-19b. In some embodiments, preparing 102B the expression vector includes preparing a plasmid vector including one or more gene fragments of the disordered polypeptides. In some embodiments, the lengths of the one or more gene fragments are then duplicated to create the nucleotide sequence encoding a 2, 4, 8, 16, 32, or 64mer of the desired disordered polypeptide. The resulting sequence can then be inserted into an expression vector. As discussed above, in some embodiments, the expression vector includes one or more exogenous nucleotide sequences encoding a disordered polypeptide, and at least one promoter regulating the expression of the one or more exogenous nucleotide sequences. At 102B', the expression vector is inserted into an E. coli strain.

As also discussed above, in some embodiments, the recombinant E. coli strain includes one or more mutations to one or more stress-response genes. In some embodiments, the one or more stress-response genes is yggw, yedv, yedw, yedy, spec, speb, uspc, hcha, loip, mltc, envz, ompr, yhgf, or hupb. In some embodiments, basal expression of the one or more exogenous nucleotide sequences in an about 0.6 to about 0.8 OD600 culture of the recombinant bacteria for about 4 hours of incubation produces less than about 70 mg/L, produces less than about 60 mg/L, produces less than about 50 mg/L, produces less than about 40 mg/L, produces less than about 30 mg/L, produces less than about 20 mg/L, less than about 10 mg/L, less than about 9 mg/L, less than about 8 mg/L, or less than about 7 mg/L disordered polypeptide in the culture. In some embodiments, basal expression of the one or more exogenous nucleotide sequences in a culture of the recombinant bacteria at about 3 hours of incubation post-inoculation produces less than about 7 mg/L.

Referring again to FIGS. 1A-1B, in some embodiments, at 104, a pLysS plasmid is inserted into SoluBL21 *E. coli*. In some embodiments, at 106A, the one or more exogenous nucleotide sequences are expressed. Referring now specifically to FIG. 1B, in an exemplary embodiment of step 106A, this expression, e.g., of the expression vector is induced 106B. In some embodiments, the expression is induced via one or more inducing agents. In some embodiments, the one or more inducing agents include isopropyl-β-D-thiogalactoside (IPTG). In some embodiments of step 106A, expression of the one or more exogenous nucleotide sequences occurs only via basal expression, i.e., expression of the one or more exogenous nucleotide sequences is not induced. As will discussed in greater detail below, in these embodiments, basal expression of the one or more exogenous nucleotide sequences under control of a "leaky" promotor can produce high titers of exogenous polypeptide without the toxicity, reduction in plasmid maintenance, etc. that can be associated with induction. As a result, embodiments of the present disclosure can produce high titers of desired product in recombinant bacteria where induced production of disordered polypeptides can be disadvantageous. In some embodiments, longer culture times in the absence of inducer are utilized to enable prolonged basal expression, which again advantageously produces high titers of desired product while minimizing disadvantageous effects of induction on some recombinant bacteria. In some embodiments, the basal expression of the one or more exogenous nucleotide sequences in culture is allowed for proceed for greater than 4, 5, 6, 7, 8, 9, 10, 15, 20 hours, etc.

Figure 2:
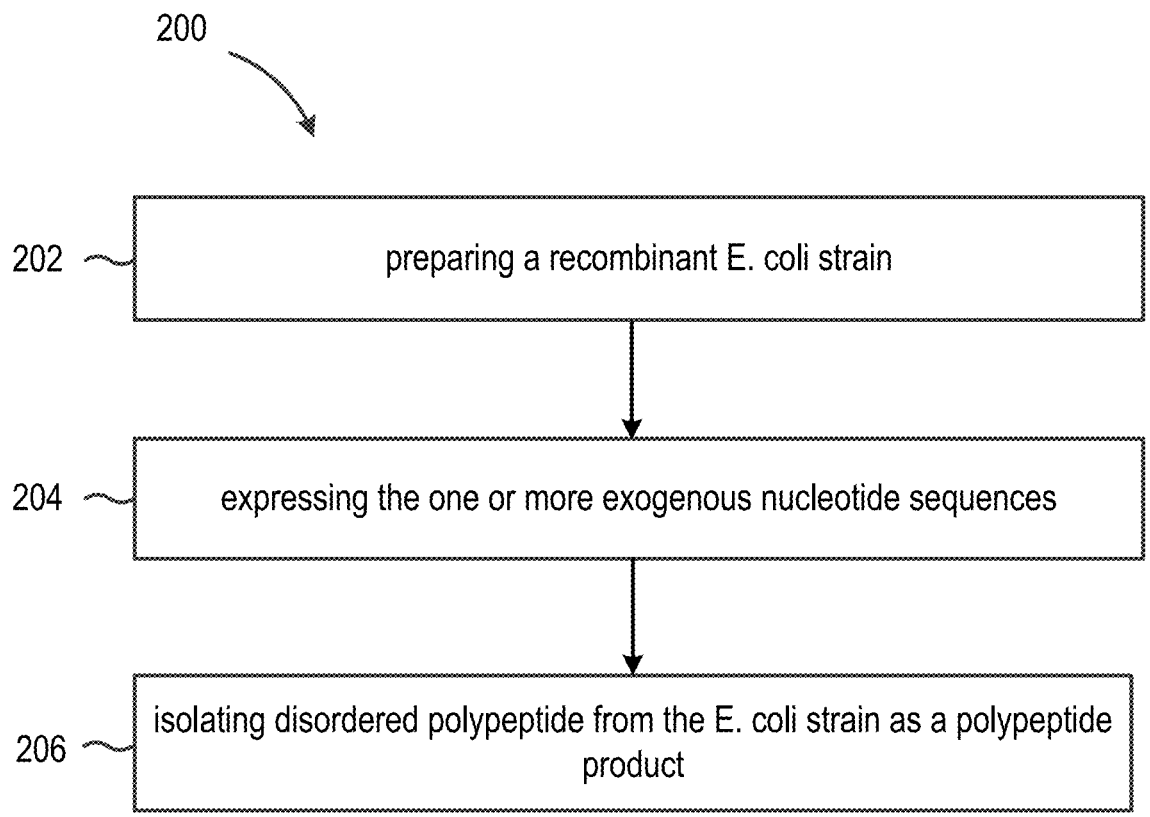
FIG. 2 is a chart of a method of producing an exogenous polypeptide product according to some embodiments of the present disclosure.

Referring now to FIG. 2, some embodiments of the present disclosure are directed to a method 200 of producing an exogenous polypeptide product. As discussed above, in some embodiments, the disordered polypeptide includes between about 20% and about 50% glycine residues. In some embodiments, the disordered polypeptide includes between about 25% and about 45% glycine residues. In some embodiments, the disordered polypeptide includes between about 30% and about 40% glycine residues. In some embodiments, the disordered polypeptide includes between about 5% and about 25% proline residues. In some embodiments, the disordered polypeptide includes between about 10% and about 20% proline residues. In some embodiments, the disordered polypeptide includes more than about 15% glutamine residues. In some embodiments, the disordered polypeptide includes more than about 20% glutamine residues. In some embodiments, the disordered polypeptide includes more than about 10% valine residues. In some embodiments, the disordered polypeptide includes more than about 15% valine residues. In some embodiments, the disordered polypeptide includes above about 0% and below about 5% tyrosine residues. Structurally, in some embodiments, the disordered polypeptide includes above about 0% and below about 35% beta sheets. In some embodiments, the disordered polypeptide includes between about 5% and about 30% beta sheets. In some embodiments, the disordered polypeptide includes between about 5% and about 20% beta sheets. In some embodiments, the disordered polypeptide includes between about 15% and about 30% beta sheets. In some embodiments, the disordered polypeptide includes between about 20% and about 75% alpha helices. In some embodiments, the disordered polypeptide includes between about 25% and about 70% alpha helices. In some embodiments, the disordered polypeptide includes between about 25% and about 50% alpha helices. In some embodiments, the disordered polypeptide includes between about 50% and about 55% alpha helices. In some embodiments, the disordered polypeptide includes between about 45% and about 70% alpha helices. In some embodiments, the disordered polypeptide includes between 0% and about 55% random coils. In some embodiments, the disordered polypeptide includes between 0% and about 50% random coils. In some embodiments, the disordered polypeptide includes between 0% and about 5% random coils. In some embodiments, the disordered polypeptide includes between 25% and about 50% random coils. In some embodiments, the disordered polypeptide includes above about 0% and below about 50% beta-turns. In some embodiments, the disordered polypeptide includes between about 5% and about 45% beta-turns. In some embodiments, the disordered polypeptide includes between about 10% and about 45% beta-turns. In some embodiments, the disordered polypeptide includes between about 20% and about 30% beta-turns. In some embodiments, the disordered polypeptide includes recombinant spidroins, ELPs, or combinations thereof.

In some embodiments, the disordered polypeptide includes a primary sequence including GPGQQ AAAAA GPGQQ GPGQQ GPGQQ GPGEQ GPGSG (SEQ. ID NO.: 1). In some embodiments, the disordered polypeptide includes a primary sequence including GPGQQ AAAAA AAAAA GPGQQ GPGQQ GPGEQ GPGSG (SEQ. ID NO.: 2). In some embodiments, the disordered polypeptide includes ELP constructs combining one or more native elastin motifs of VPGAG with specific placement of tyrosine and GRGDS domains for targeted neurological drug delivery. In some embodiments, the disordered polypeptide includes a primary sequence including: (VPGAGVP-GAGVPGAGVPGAGVPGYGVPGAGVPGAGVP-GAGVPGAGVPGYG)2 GRGDS (SEQ. ID NO.: 3). In some embodiments, the disordered polypeptide is based on two or more distinct and purposefully designed monomers. In some embodiments, the disordered polypeptide is based on two or more distinct and purposefully designed monomers which are duplicated one or more times. In some embodiments, the disordered polypeptide includes a 2, 4, 8, 16, 32, or 64mer of the primary sequence.

At 202, a recombinant *E. coli* strain is prepared. As discussed above, in some embodiments, the recombinant *E. coli* strain includes an expression vector. In some embodiments, the expression vector includes one or more exogenous nucleotide sequences encoding a disordered polypeptide. In some embodiments, the expression vector includes at least one promoter regulating the expression of the one or more exogenous nucleotide sequences.

As also discussed above, in some embodiments, the recombinant *E. coli* strain includes one or more mutations to one or more stress-response genes. In some embodiments, the one or more stress-response genes is yggw, yedv, yedw, yedy, spec, speb, uspc, hcha, loip, mltc, envz, ompr, yhgf, or hupb. In some embodiments, basal expression of the one or more exogenous nucleotide sequences in an about 0.6 to about 0.8 OD600 culture of the recombinant bacteria for about 4 hours of incubation produces less than about 70 mg/L, produces less than about 60 mg/L, produces less than about 50 mg/L, produces less than about 40 mg/L, produces less than about 30 mg/L, produces less than about 20 mg/L, less than about 10 mg/L, less than about 9 mg/L, less than about 8 mg/L, or less than about 7 mg/L disordered polypeptide in the culture. In some embodiments, basal expression of the one or more exogenous nucleotide sequences in a culture of the recombinant bacteria at about 3 hours of incubation post-inoculation produces less than about 7 mg/L.

At 204, the one or more exogenous nucleotide sequences are expressed. As discussed above, in some embodiments, expression 204 of the one or more exogenous nucleotide sequences includes induction via application of one or more inducing agents. In some embodiments, the one or more inducing agents includes IPTG. In other embodiments, the expression of the one or more exogenous nucleotide sequences is basal expression, e.g., in the absence of inducing agent. As discussed above, in some embodiments, longer culture times in the absence of inducer are utilized. In some embodiments, the basal expression of the one or more exogenous nucleotide sequences in culture is allowed for proceed for greater than 4, 5, 6, 7, 8, 9, 10, 15, 20 hours, etc. At 206, the disordered polypeptide is isolated from the *E. coli* strain as a polypeptide product. Isolation 206 of the polypeptide product is performed via any suitable process, e.g., cellular secretion, cellular lysis and subsequent isolation via decanting, centrifugation, chromatography, membrane separation, etc., or combinations thereof.

Exemplary recombinant bacteria were prepared consistent with the embodiments described above and compared to 9 commercially available *E. coli* strains: BL21, BL21 pLysS, RosettaGami B, BL21 pGro7, BLR, HMS174, MG1655, SoluB21, and Origami B. Some strains were chosen based on factors previously shown or hypothesized to affect recombinant silk production, such as codon usage and inclusion body formation. These strains include RosettaGami B, which has upregulation of seven tRNAs for rare codons including those for glycine and proline, as well as BLR, which has a recA-mutation that may facilitate increased stability of plasmids containing repetitive sequences. The strain SoluBL2 has been developed through directed evolution to produce soluble protein when its ancestral strain, BL21(DE3), does not yield detectable soluble product. Likewise, strain pGro7 expresses a chaperone protein that prevents inclusion body formation and promotes soluble production. Strains HMS 174 and MG1655, which unlike other strains tested, are from the K-12 *E. coli* lineage instead of the B lineage. Strain pLysS restricts basal expression, while strain Origami B includes mutations that change the cytoplasmic environment and cellular stress responses through alterations to the thiol-redox equilibrium, glutathione metabolism, and oxidative stress response. All strains were DE3 lysogens and proteins were expressed from the pET19b vector under control of the T7 promoter.

Four different de novo designed spidroin constructs were expressed in these *E. coli* stains, with titer, plasmid maintenance, and OD600 measured as expression outcomes. The primary sequences and polymeric structure of the spidroin constructs are depicted in Table 2 below:

TABLE 2

Primary Sequence of Recombinant Spidroin Constructs

| Spidroin Construct | Primary Sequence | Number of Repeats | Molecular Weight (kDa) |
|---|---|---|---|
| A5 4mer | MGHHHHHHHHHHSSGHIDDDDKHMLEHMPG (GPGQQAAAAAGPGQQGPGQQGPGQQGPGEQGPGSG)n TSGS (SEQ. ID NO.: 4) | n = 4 | 16.1 |
| A5 16mer | MGHHHHHHHHHHSSGHIDDDDKHMLEHMPG (GPGQQAAAAAGPGQQGPGQQGPGQQGPGEQGPGSG)n TSGS (SEQ. ID NO.: 5) | n = 16 | 52.7 |
| A10 4mer | MGHHHH IHHHHSSGHIDDDDKHMLEHMPG (GPGQQAAAAAAAAAAGPGQQGPGQQGPGEQGPGSG)n TSGS (SEQ. ID NO.: 6) | n = 4 | 15.6 |
| A10 16mer | MGHHHHH HHHHHSSGHIDDDDKHMLEHMPG (GPGQQAAAAAAAAAAGPGQQGPGQQGPGEQGPGSG)n TSGS (SEQ. ID NO.: 7) | n = 16 | 50.9 |

To assess the effect of protein size, recombinant spidroins were designed to have either four or sixteen identical monomer units in tandem (referred to as 4mers and 16mers, respectively). To assess the effect of modulating primary sequence, two different monomer units of 35 amino acids were designed, with one containing a segment of five tandem alanine residues (A5) and the other a segment of ten tandem alanine residues (A10). The remaining amino acids in the monomer sequences included multiple GPGQQ motifs (four for the A5 monomer and three for the A10 monomer) and single GPGEQ and GPGSG motifs. Both monomer units were designed based on naturally occurring primary sequences found in the MaSp2 dragline spidroin of orb-weaving spiders. Modulating the tandem alanine length and total construct length were chosen as focal points to demonstrate the effect of construct design on expression outcomes. All constructs expressed had a starting sequence that is present on the pET-19b expression vector, which contains a 10× histidine tag for purification followed by an enterokinase cleavage sequence.

Figure 3A:
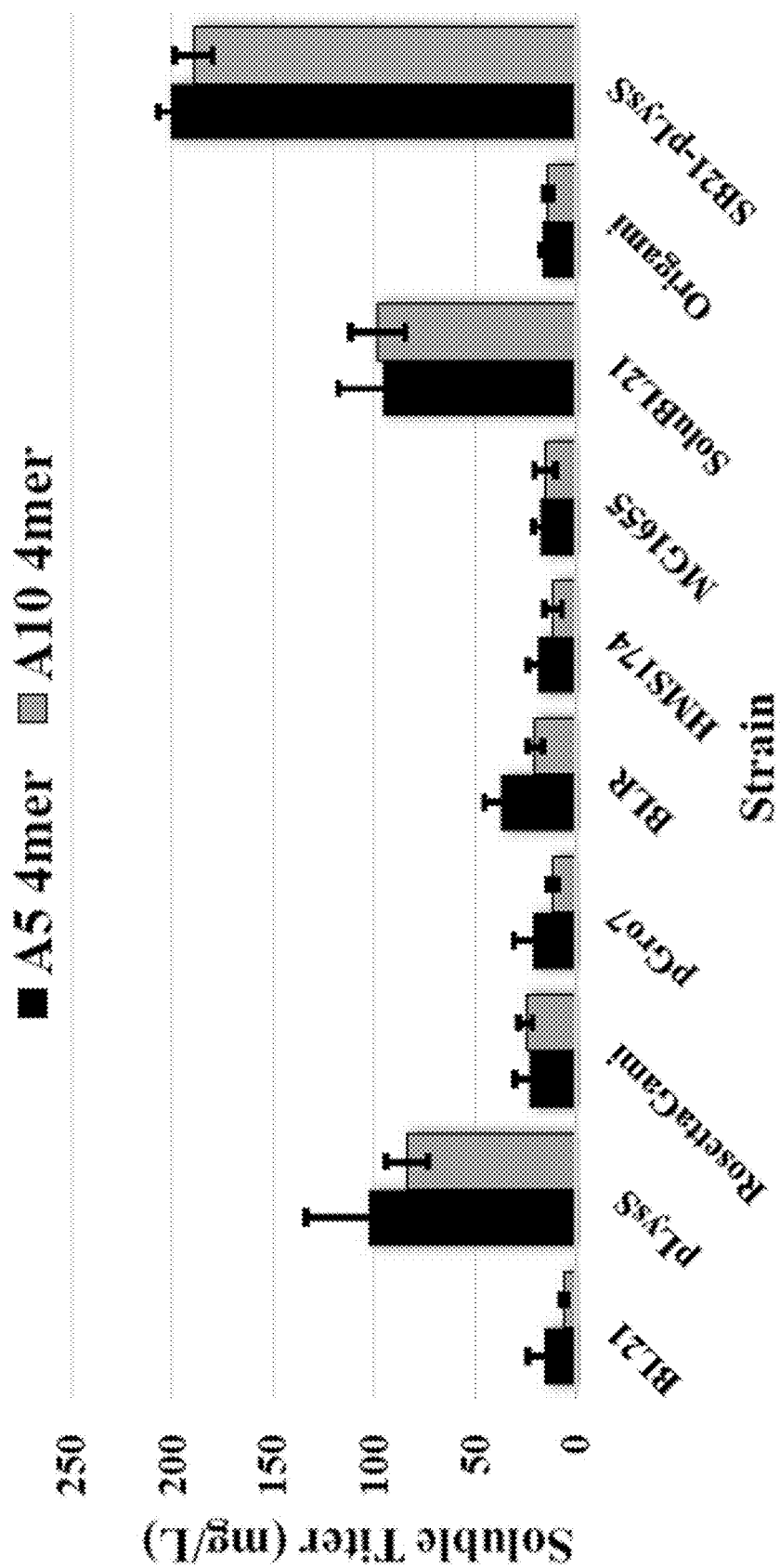
FIGS. 3A-3B is a graph showing soluble titer for recombinant spidroins produced by ten strains of E. coli in Luria-Bertani (LB) media.
Figure 3B:
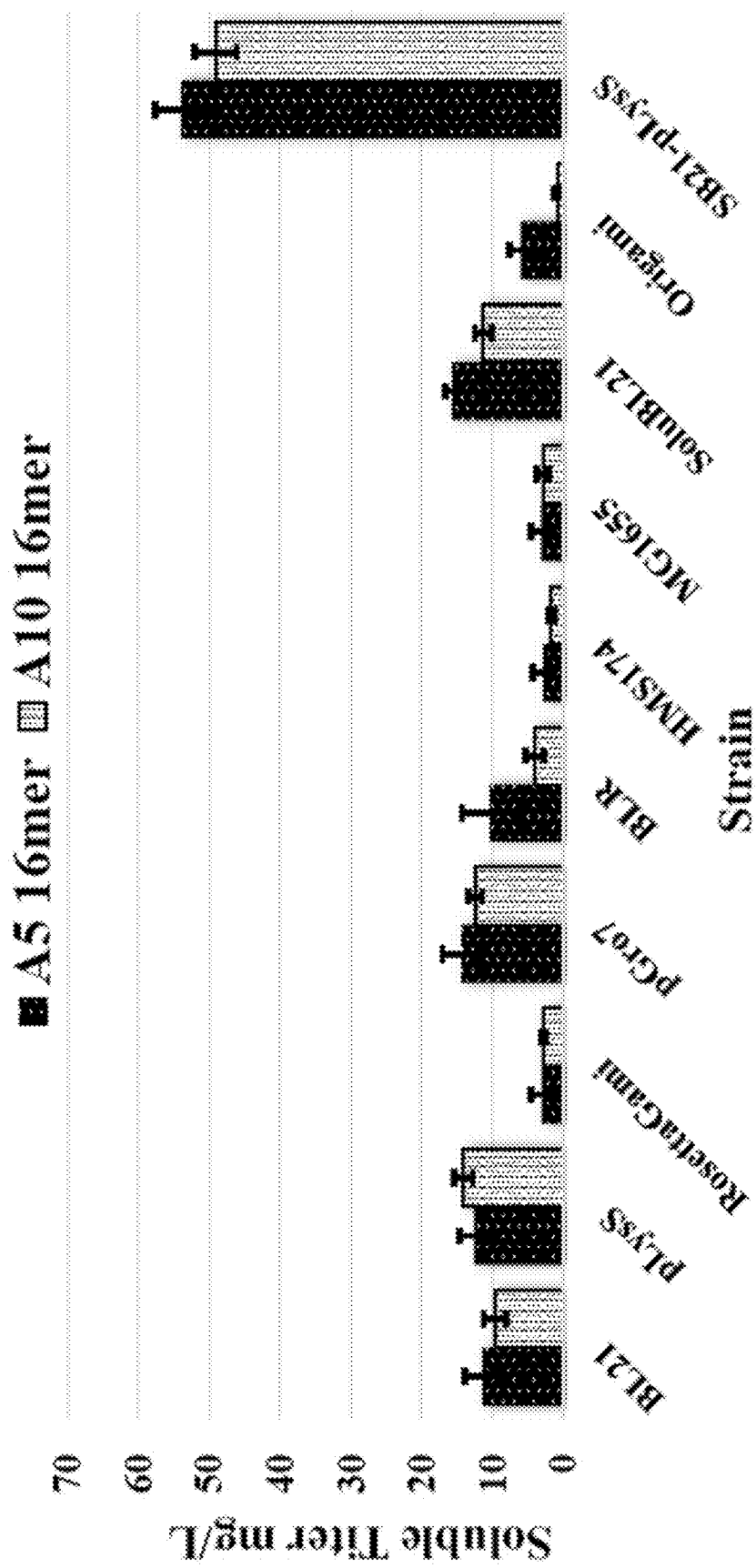

Referring to FIGS. 3A-3B, expression of the A5 and A10 constructs took place in LB media at 37° C. for four hours. pLysS and SoluBL21 were found to have higher production levels for the smaller recombinant spidroins (A5 4mer and A10 4mer). These strains yielded approximately 80-100 mg/L of A5 and A10 4mer protein, producing at levels several times above the other strains (see FIG. 3A).

In this exemplary embodiment, the pLysS plasmid from the pLysS strain was extracted and transformed into SoluBL21, referred to hereinafter as "SoluBL21-pLysS." The hybrid strain was able to produce the small spidroins at 201 (±6) and 189 (±10) mg/L for the A5 4mer and A10 4mer, respectively. These titers were approximately twice that of either parent strain. Moreover, when compared to BL21, these titers represented a 13-fold increase for the A5 4mer and a 33-fold increase for the A10 4mer (see FIG. 3A). The titers for both the A5 and A10 16mers were lower than that of the 4mers for nearly all strains, which is consistent with previous findings showing an inverse relationship between yield and spidroin length. Despite displaying some of the highest titers for the 16mers, at 11-15 mg/L, strains pLysS and SoluBL21 showed no appreciable advantage over BL21, pGro7, or BLR, which all yielded similar titers (see, e.g., FIG. 3B). The SoluBL21-pLysS hybrid strain outperformed both of its parent strains for producing the G6mers, with titers of 53 (±4) and 49 (±3) mg/L for the A5 6mer and A10 16mer, respectively. This is approximately a four-fold increase in 16mer titer versus the parent strains. Several strains, including RosettaGami, HMS174, MG1655, and Origami B were barely capable of producing detectable levels of the 16mers, as shown by titers of 5 mg/L or less.

Figure 4:
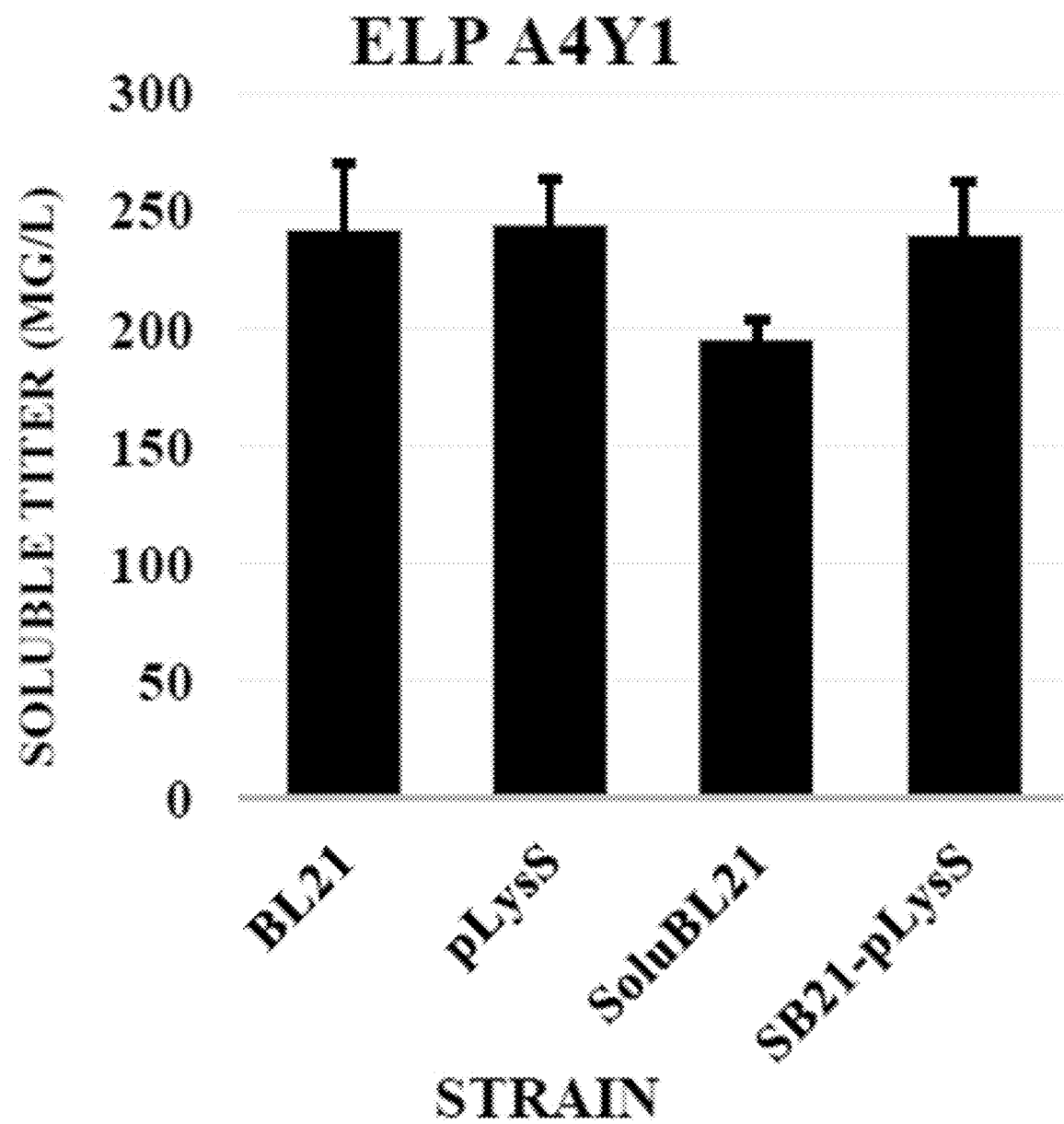
FIG. 4 is a graph showing titer of A4Y1 elastin-like peptide (ELP) in BL21, pLysS, SoluBL21, and SoluBL21-pLysS (SB21-pLysS) E. coli strains.

To demonstrate the increased spidroin titers achieved with the hybrid SoluBL21-pLysS strain could be extended to other repetitive, structural proteins, an ELP was produced in strains BL21, pLysS, SoluBL21, and SoluBL21-pLysS. The recombinant ELP, A4Y1, was chosen for production in these four strains based on structural similarity when compared to the A5 4mer primary sequence, as shown in Table 3 below:

Referring now to FIG. 4, strains pLysS, SoluBL21, and SoluBL21-pLysS offered no advantage over BL21 for the titer of the ELP construct. The soluble titers for these three strains were similar at ~240 mg/L. SoluBL21 performed the worst out of the four strains with a titer of 196 (±8) mg/L. In all cases, the A5, A10, and ELP constructs were expressed primarily in the soluble fraction of the lysate, with only negligible amounts found in the pellet (<2 mg/L for all strains). Notably, the titer for the ELP in BL21 is over 15 times higher than for the A5 4mer under the same expression conditions, unexpected when considering the high degree of similarity between the A5 4mer and the A4Y1 ELP.

Figure 5A:
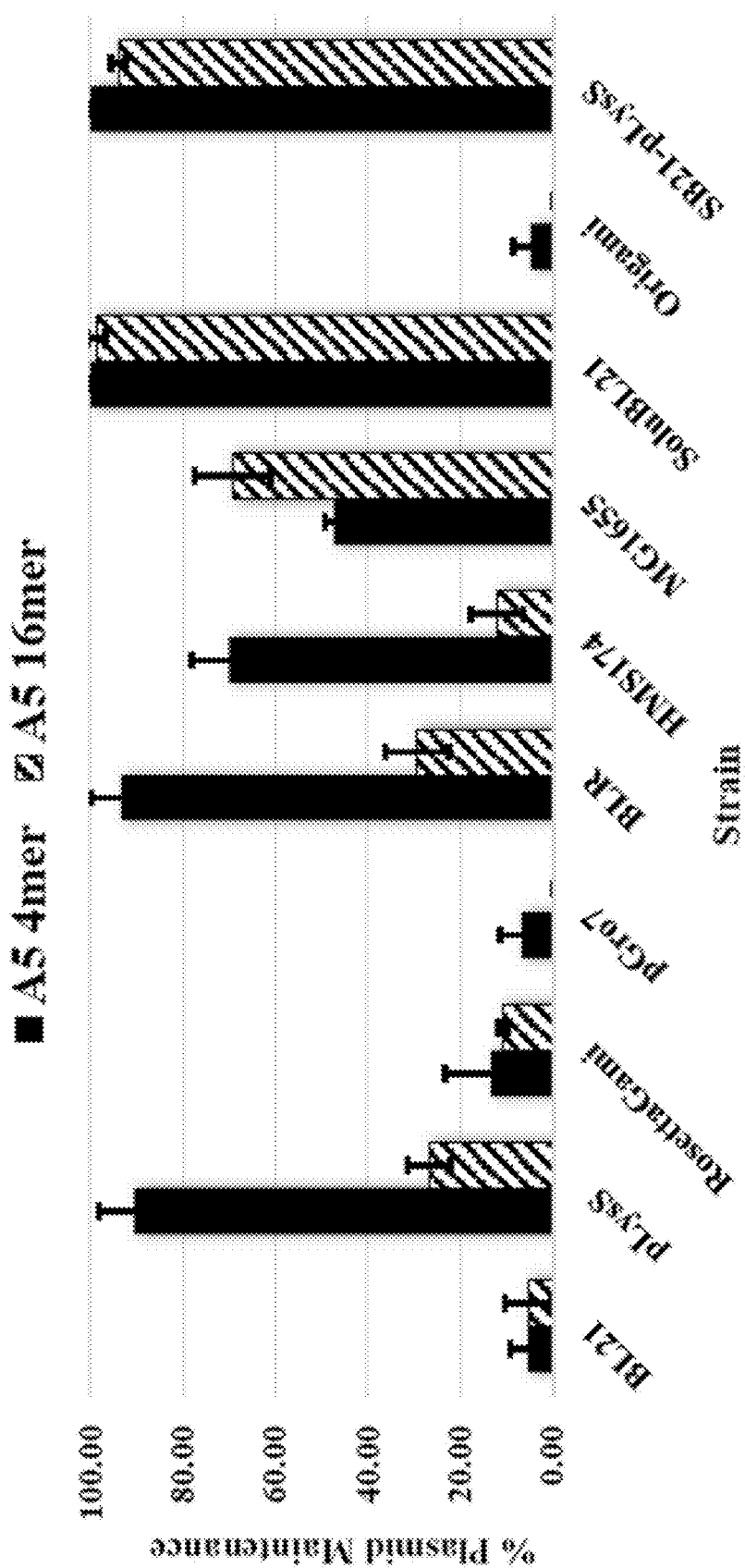
FIGS. 5A-5B are graphs showing plasmid maintenance of recombinant spidroins A5 4mer, A5 16mer, A10 4mer, and A10 16mer in E. coli strains at the end of a four-hour expression in LB media.
Figure 5B:
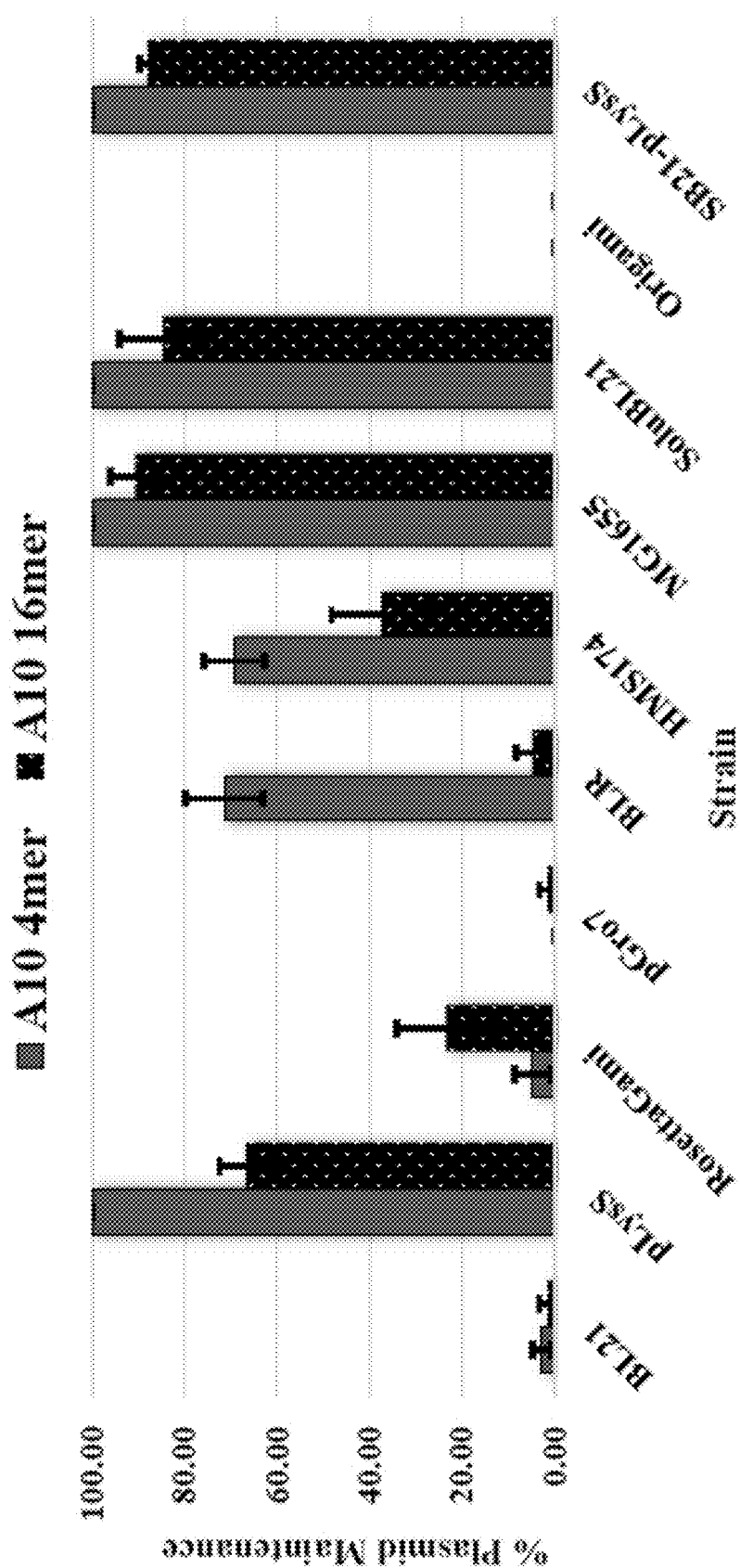
Figure 5C:
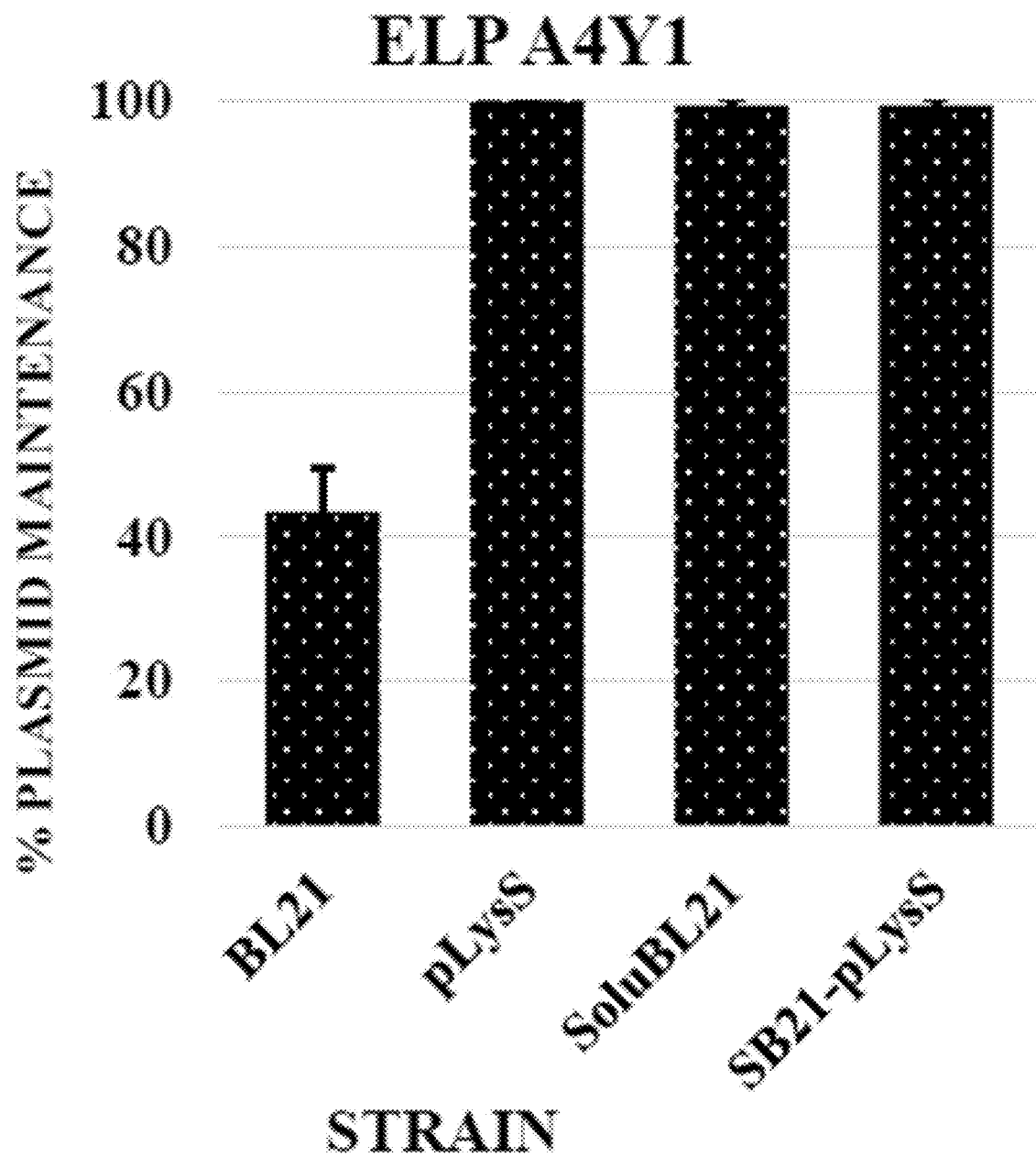
FIG. 5C is a graph showing plasmid maintenance of the ELP construct in E. coli strains BL21, pLysS, SoluBL21, and SoluBL21-pLysS (SB21-pLysS) at the end of a four-hour expression in LB media.

During exogenous polypeptide expression, cells can potentially lose the plasmid vector that was transformed into them. Plasmid loss is indicative of excessive metabolic burden, which may stem from repetitive recombinant DNA sequences or toxic recombinant protein products and exacerbated by depletion of antibiotic selection factors. Plasmid-free cells can continue to divide, leading to a substantial decrease in the overall number of cells in a culture that are producing recombinant protein. A high level of plasmid maintenance contributes to the achievement of high titers, particularly for high-density cell cultivation in bioreactors. FIGS. 5A-5B show the plasmid maintenance of the A5 and A10 constructs in the ten *E. coli* strains, and FIG. 5C shows the plasmid maintenance of the ELP construct in BL21, pLysS, SoluBL21, and SoluBL21-pLysS. Both figures represent the plasmid maintenance at the end of a four-hour expression in LB media. FIGS. 5A-5B show that plasmid maintenance decreased for most strains when expressing a 16mer construct compared to a 4mer construct. Although plasmid maintenance of the 16mers decreased substantially for pLysS compared to the 4mers, the hybrid strain main-

TABLE 3

A5 4mer and A4Y1 ELP Primary Sequences and Amino Acid Composition

| Protein | Sequence | Glycine % | Proline % | Alanine % | Glutamine % | Valine % | Tyrosine % |
|---|---|---|---|---|---|---|---|
| A5 4mer (MW: 16 kDa) | MGHHHHHHHHHHSSGHI DDDDKHMLEHMPG (GPGQQAAAAAGPGQQGP GQQGPGQQGPGEQGPGSG)n TSGS (SEQ. ID NO.: 4) | 32 | 14 | 12 | 21 | 0 | 0 |
| A4Y1 ELP (MW: 16 kDa) | MGHHHHHHHHHHSSGHI DDDDKHMLEHM VPGAGVPGAGVPGAGVPG AGVPGYGVPGAGVPGAG VPGAGVPGAGVPGYGGRG DSVPGAGVPGAGVPGAGV PGAGVPGYGVPGAGVPGA GVPGAGVPGAGVPGYGGR GDSVPGAGVPGAGVPGAG VPGAGVPGYGVPGAGVPG AGVPGAGVPGAGVPGYG (SEQ. ID NO.: 8) | 35 | 16 | 13 | 0 | 16 | 3 |

The A5 4mer and the A4Y1 ELP both have a 4mer polymeric structure, along with similar molecular weight and glycine, proline, and alanine contents. Furthermore, both recombinant spidroins and ELPs self-assemble into supramolecular materials when triggered by external stimuli. However, the A5 4mer has tandem alanines ($A_n$) while the ELP has alanine residues distributed throughout the construct. Additionally, the A5 4mer has a high amount of glutamine (21%), which the ELP lacks, and the ELP has a high percentage of valine (16%) and some tyrosine (3%), both of which are missing from the A5 4mer.

tained the ability of SoluBL21 to maintain these 16mer vectors at 85% or above. Without wishing to be bound by theory, this data suggests that a high titer of recombinant spidroin benefits from high plasmid maintenance. The strains that yielded the highest titers of the 4mer proteins, namely pLysS, SoluBL21, and SoluBL21-pLysS, all exhibit a plasmid maintenance of 90% or higher. Likewise, the strain that yielded the highest titers for the 16mers, SoluBL21-pLysS, exhibited one of the highest overall plasmid maintenance levels for the 16mers. For the BL21, RosettaGami, pGro7, and Origami strains, there was nearly a complete loss of the plasmid during spidroin expression. In contrast, FIG. 5C shows that strain BL21 exhibited a plasmid maintenance of 43% during the ELP expression, which is over 14 times higher than maintenance during the expression of the A5 4mer or any other spidroin. This is in accordance with the 15 times higher level of production that BL21 was able to achieve for the ELP versus the A5 4mer. The strains pLysS, SoluBL21, and SoluBL21-pLysS exhibited levels of plasmid maintenance for the ELP at or near 100%, similar to their behavior during spidroin expressions.

Figure 6A:
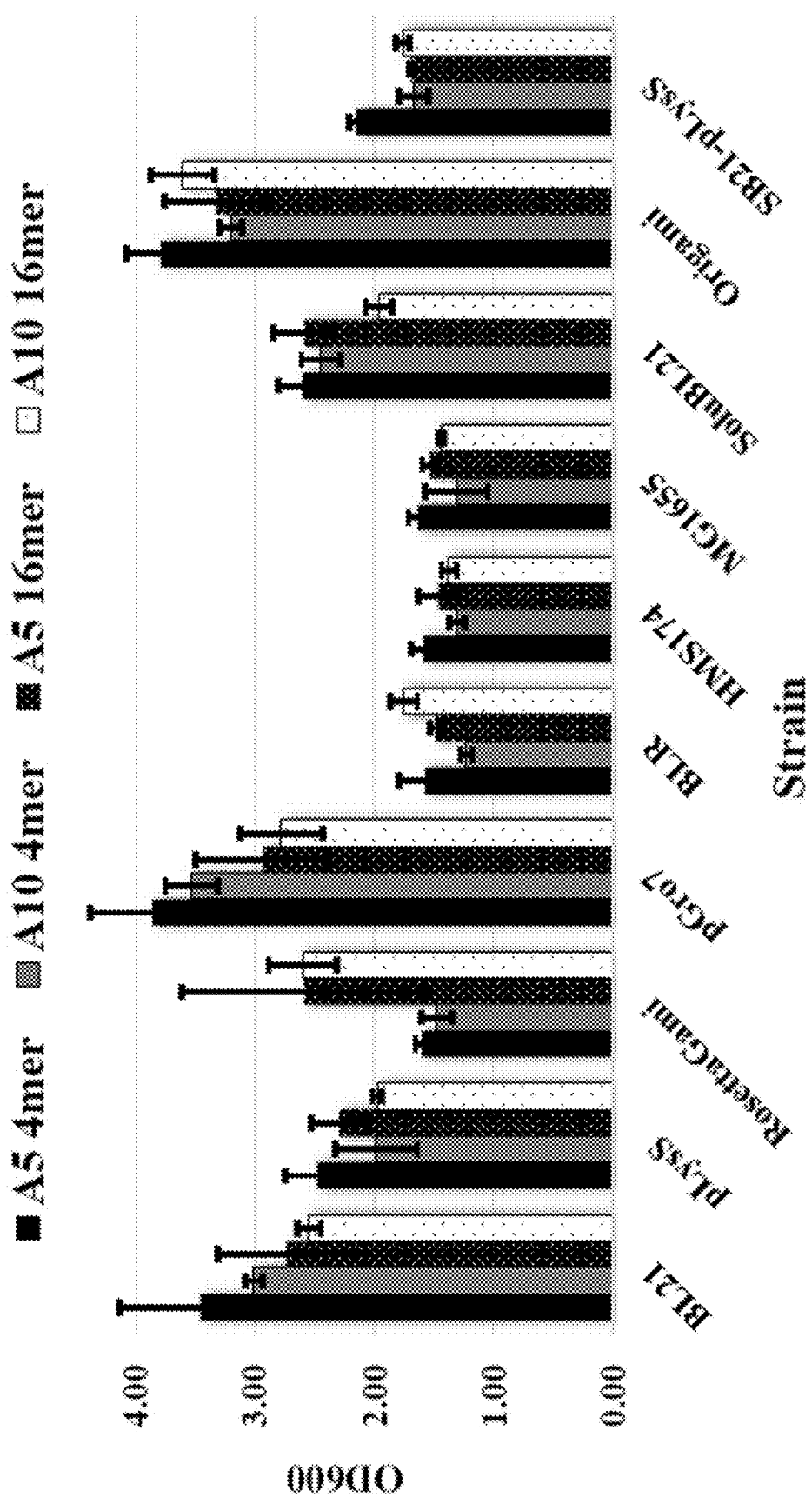
FIG. 6A is a graph showing OD600 of E. coli cultures before and after a four-hour expression therein of the A5 4mer, A5 16mer, A10 4mer, and A10 16mer constructs.

Referring to FIG. 6A, cell growth over a four-hour expression of the four different spidroin constructs was investigated. While all cultures were induced for protein expression at an OD600 of 0.6-0.8, the final OD600 at the end of the four-hour expression was highly variable among the strains, ranging from 1.58-3.86. The high-producing strains, pLysS, SoluBL21, and SoluBL21-pLysS, showed final OD600s that were at or near the median of the dataset obtained for the ten strains (median of 2.07). The OD600 at the end of a four-hour expression did not show an obvious relationship to spidroin titer, as strains with poor titers showed both higher and lower final OD600s than pLysS, SoluBL21, and SoluBL21-pLysS. Strains BL21, pGro7, and Origami B, which grew the most during spidroin expression by routinely reaching final OD600s of above 3, were also the strains that showed the lowest levels of plasmid maintenance in addition to low titers. Without wishing to be bound by theory, this is likely due to the degradation of ampicillin in the media, which allows non-plasmid bearing cells that are potentially fitter to proliferate. This phenomenon is particularly applicable in cases where the recombinant construct is harmful or toxic to the cells and can be further exacerbated by using ampicillin over other antibiotics as the selection pressure since the product of the beta-lactamase gene conferring resistance to ampicillin is secreted, with studies showing that rapid plasmid loss and growth of non-plasmid bearing cells can be difficult to prevent, even in cases where additional ampicillin is added to the culture. Thus, the increased growth rates of strains that have lost the vector and produce little silk protein suggest that expression of the A5 and A10 spidroins exert toxicity on the cells.

The possibility that expressing A5 and A10 spidroins causes host cell toxicity was further supported by observations made during the plasmid maintenance assay, in which 0.1 ml of a 10,000× culture dilution (generated through serial dilutions) was plated for colony counting. For most strains observed, this procedure resulted in several hundred single colonies on LB agar plates. However, the strains that showed moderate to high levels of plasmid maintenance but low titers and inhibited growth after induction (RosettaGami, BLR, HMS174, and MG1655) displayed a lack of colony forming units on LB plates using this protocol. Compared to other strains at the same OD600, cultures of RosettaGami, BLR, HMS174, and MG1655 used a 100× (instead of a 10,000×) dilution of a culture sample to obtain enough isolated colonies for the plasmid maintenance assay (minimum of 50 colonies). This lack of colony-forming-units after recombinant protein induction is a documented effect of toxic protein expression in cases where the vector is still maintained.

Figure 6B:
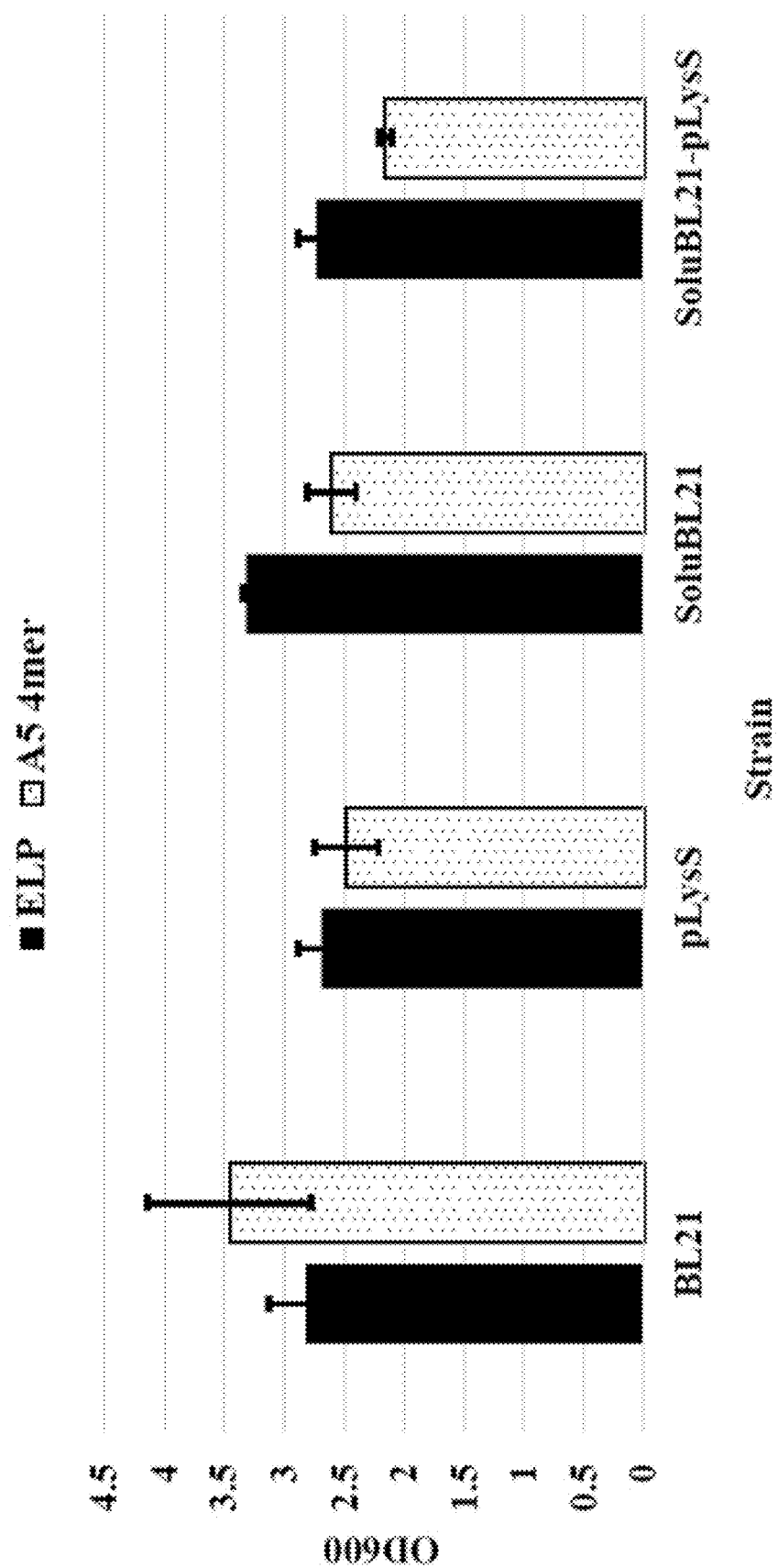
FIG. 6B is a graph showing OD600 at the end of a four-hour expression for the A5 4mer and ELP constructs in E. coli strains BL21, pLysS, SoluBL21, and SoluBL21-pLysS.

Referring now to FIG. 6B, the toxicity effect from the spidroins can be seen at the final OD600 for cells expressing ELP as compared with A5 4mer. The final OD600 at the end of a four-hour expression for the ELP was higher for pLysS, SoluBL21, and SoluBL21-pLysS (+0.22, 0.72, 0.575, respectively), even with a higher titer of ELP than A5 4mer. Protein overexpression at a high level, independent of the toxicity of the construct, can be associated with decreases in cell growth.

Figure 6C:
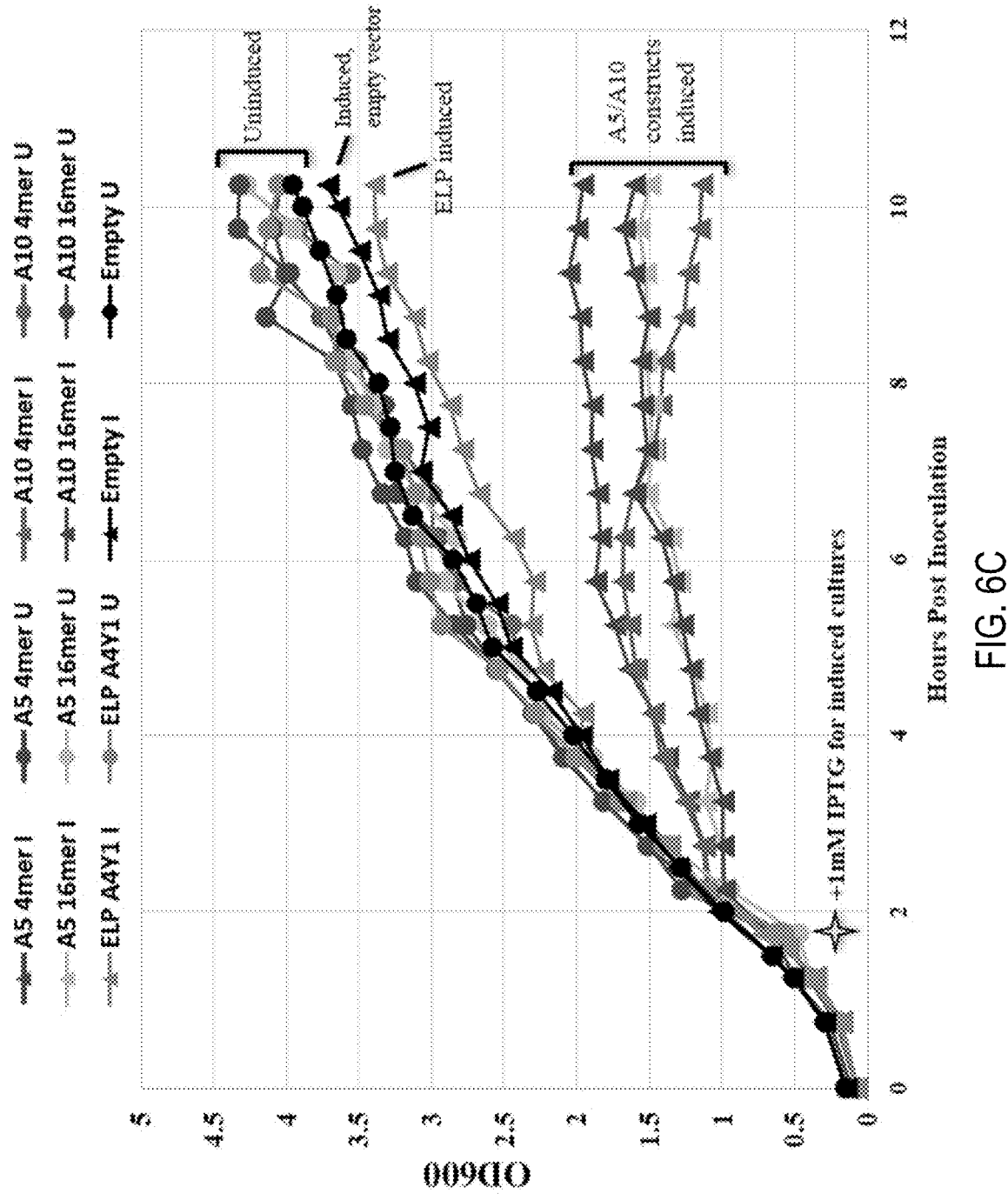
FIG. 6C is a graph showing OD600 of SoluBL21-pLysS in LB media.

Referring now to FIG. 6C, growth under a variety of conditions for strain SoluBL21-pLysS was measured in LB media for 10.25 hours under a variety of conditions and starting from the point of inoculation (2% v/v inoculum from an overnight culture). The uninduced cultures and empty vector controls reach a late exponential or early stationary phase after 10.25 hours and at an OD600 of approximately 3.72-4.18. The cultures induced for ELP production follow these curves closely in both rate of growth and overall growth, as there is no significant decrease in the slope of the curve after induction, and the final OD600 of 3.42 is only an 8% decrease from that of the induced empty vector control (3.72). ELP expression does not appear to significantly affect cell health and fitness, even at titers above 200 mg/L. However, when expressing an A5 or A10 spidroin, there is a significant decrease in the slope of the growth curve directly after induction at 1.75 hours. Then, a stationary phase is reached up to 5 hours sooner and the final OD600 decreases on average by −61% and −57% when compared to the uninduced or induced empty vector controls, respectively. When expressing the A10 4mer, there is potentially a death phase (consistent decrease in OD600) that begins approximately 4 hours after induction. As can be seen, the exemplary embodiments of the present disclosure are effective to produce toxic polypeptides such as recombinant silk, and further is able to maintain growth cell growth even during the expression of disordered ELPs.

Without wishing to be bound by theory, the disordered nature of the spidroin constructs is a factor underlying their toxicity, low titers, and low plasmid maintenance. This toxicity may result from promiscuous and harmful binding interactions by disordered proteins within the intracellular milieu. As recombinant MaSp2-mimetic spidroins can be high in disorder-promoting amino acids (proline, glutamine, glycine, serine) and low in order-promoting amino acids, the recombinant bacteria of the present disclosure are advantageous in their ability to produce high titers of recombinant spidroins without experiencing these toxic effects. The hybrid SoluBL21-pLysS strain showed substantially improved recombinant spidroin expression compared to other E. coli strains (see again FIGS. 3A-3B).

To demonstrate the underlying cellular mechanisms of this exemplary embodiment, basal expression of the recombinant nucleotides was examined. As discussed above, basal expression refers to the expression of a recombinant gene without induction, which can cause plasmid loss and subsequent low titers if the gene product is toxic. In this exemplary embodiment, SoluBL21-pLysS exerts tight control over basal expression via production of T7 lysozyme, which inhibits action of T7 polymerase and prevents basal expression of recombinant genes placed on pET vectors. Upon addition of IPTG, T7 polymerase concentration increases and overcomes the inhibition of T7 polymerase.

Figure 7A:
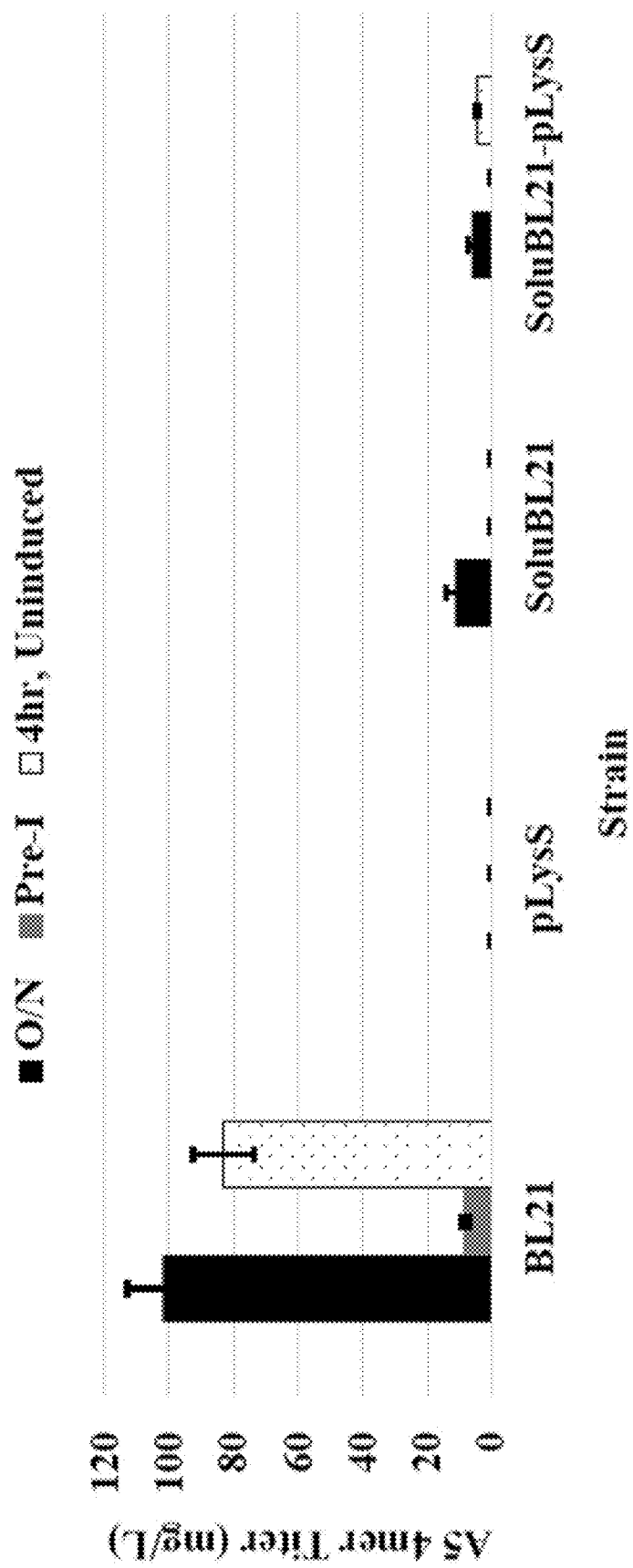
FIG. 7A is a graph showing basal expression of A5 4mer construct in E. coli strains BL21, pLysS, SoluBL21, and SoluBL21.

Referring now to FIG. 7A, basal expression was strongly restricted in strains pLysS and SoluBL21-pLysS, showing either an absence or low levels (<7 mg/L) of A5 4mer protein expression from an overnight culture grown without IPTG. Basal expression was also attenuated in strain SoluBL21, although slightly less so than for the aforementioned strains (11 (±3) mg/L from an overnight culture without IPTG). Strain BL21 exhibited copious basal expression, with overnight cultures lacking any IPTG induction yielding an average A5 4mer titer of 102 (±11) mg/L. Cultures of BL21 inoculated from an overnight culture and grown to OD600 of 0.6-0.8 also showed basal expression at 8 (±1) mg/L. Moreover, when the strain was put through the four-hour expression protocol, save for the addition of IPTG, the titer was 83 (±9) mg/L. These basal expression titers for the A5 4mer in BL21 are approximately equal to the induced expressions of the pLysS and SoluBL21 strains, however, they are only half of what the high-performance SoluBL21-pLysS strain yielded.

Figure 7B:
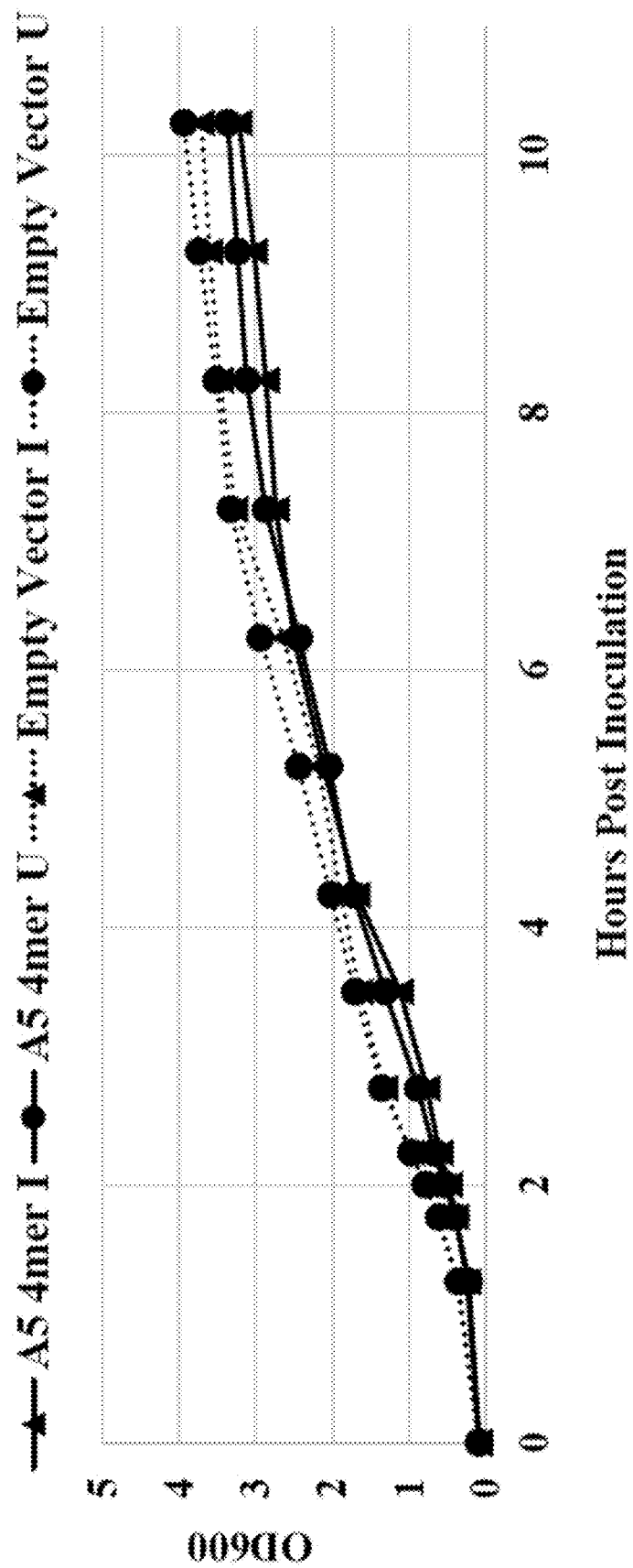
FIG. 7B is a graph showing an A5 4mer construct basal expression growth curve for E. coli strain BL21.
Figure 8:
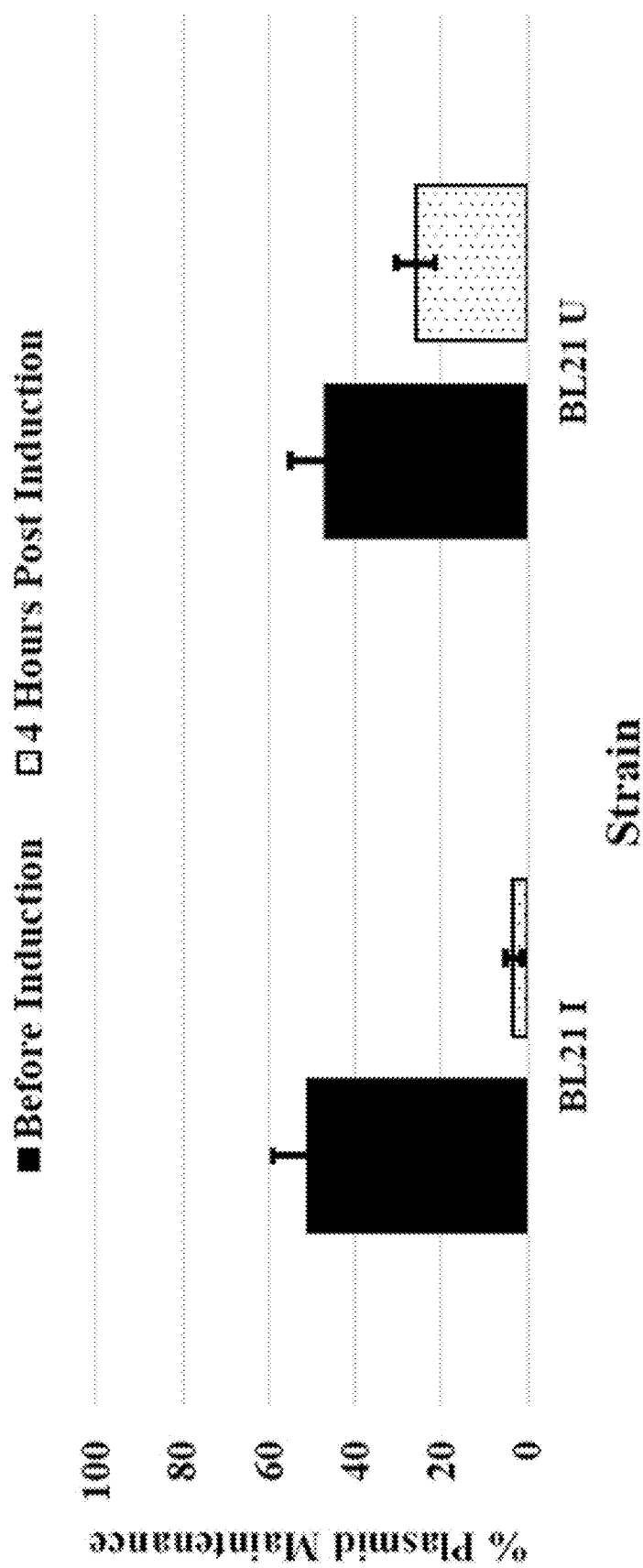
FIG. 8 is a graph showing plasmid maintenance by E. coli strain BL21 with and without induction of A5 4mer construct expression.

Referring now to FIG. 7B, growth curves for strain BL21 give further insight into the effect of basal spidroin expression. OD600 was monitored over 10.25 hours for the strain under a variety of conditions, including growth with and without inducing agent and empty vector controls. Basal expression of the A5 4mer construct had almost no negative effect on the growth of the BL21 strain when compared to controls, even though 83 (±9) mg/L of A5 4mer protein had accumulated intracellularly by 6.75 hours into the experiment. The induced BL21 strain showed no significant deviation in growth from the uninduced curves, however the titer at 6.75 hours total culture time (4 hours post induction with 1 mM IPTG) was only 15 (±8) mg/L. Thus, the BL21 strain produced approximately 5.5 times more silk protein when it is not induced with IPTG. FIG. 8 shows that this outcome is likely a result of changes in plasmid maintenance in response to induction. The plasmid maintenance at 2.75 hours (directly before induction) for both uninduced and induced strains are roughly the same (50%), albeit low due to the basal expression of a toxic gene. However, after induction with 1 mM IPTG, the plasmid maintenance of the induced culture decreased to just 3% after four hours while the uninduced maintained the vector at 26%. Thus, the strength of the promoters used in the recombinant bacteria of the present disclosure enables the successful production of toxic recombinant spidroins. In uninduced conditions, the BL21 strain is already expressing the recombinant silk gene, meaning that subsequent additions of IPTG may overwhelm cellular machinery beyond its ability to handle toxic protein expression, causing severe plasmid loss, and low titers. Likewise, since the pLysS, SoluBL21, and SoluBL21-pLysS strains do not exhibit much basal expression they exhibit high plasmid maintenance and are likely more tolerant of the increase in promoter activity caused by IPTG.

Sequencing of the recombinant bacterial strain of the exemplary embodiment revealed a number of mutations that differentiate it from *E. coli* BL21. Mutations were identified on 47 genes in the SoluBL21 genomic material of the exemplary embodiment. Of these, there are 14 genes with mutations that are directly involved in stress responses in *E. coli*. These genes include yggw, yedv, yedw, yedy, spec, speb, uspc, hcha, loip, mltc, envz, ompr, yhgf, hupb. Referring again to Table 1, these genes play roles in stress responses pertaining to heat, reactive oxygen species, cell surface damage, salt changes, acid exposure, carbonyls, osmotic changes, putrescine production, nutrient starvation, ethanol exposure, radiation, and the SOS response. Several of the mutations occur on genes responsible for extensive and broad stress pathway signaling within *E. coli*. This includes the envz/ompr two-component system, in which a mutation on the envz gene causes constant phosphorylation of the ompr transcriptional regulator. This results in a decreased repression of several stress response pathways, including those related to osmotic and acid stress. Furthermore, mutations in the spec and speb genes may alter putrescine production pathways, with putrescine production representing a way that several organisms, including *E. coli*, respond to a myriad of harmful conditions. Likewise, the uspc gene potentially promotes a more favorable cell phenotype in response to silk protein production, as uspc is induced by a diversity of stress factors that include nutrient starvation (of multiple types), oxidative stress, DNA damage, radiation, heat shock, and ethanol exposure.

There were also mutations in the DNA-binding region of hupb, a transcriptional factor that controls expression of 8% of the entire genome in regions where the genes are associated with adaptations to harsh environments, including the SOS response system, and oxidative and radiative stress systems. These mutations promote a cell phenotype that is more tolerant to the expression of disordered and potentially toxic proteins.

Nonrepetitive terminal domains are present in natural spidroins, typically 100-200 amino acids in length, and promote solubility and controlled self-assembly of recombinant spidroins. An exemplary embodiment of the present disclosure was prepared to demonstrate the use of terminal domains on increasing titers and decreasing toxicity. cDNA copies of the terminal regions of *L. hesperus* (western black widow) MaSp1 dragline silk were inserted at either end of the A10 4mer gene to form the A10 4mer BWT construct shown below:

(SEQ. ID NO.: 9)
MGHHHHHHHHHHSSGHIDDDDKHMLEHMQANTPWSSKANADAFINSFISA

ASNTGSFSQDQMEDMSLIGNTLMAAMDNMGGRITPSKLQALDMAFASSVA

EIAASEGGDLGVTTNAIADALTSAFYQTTGVVNSRFISEIRSLIGMFAQA

SANDVYASAGSSGGGYGASSASAASASAAAPSGVAYQAPAQAQISFTLR

GQQPVSGPGQQAAAAAAAAAGPGQQGPGQQGPGEQGPGSGGPGQQAAAA

AAAAAAGPGQQGPGQQGPGEQGPGSGGPGQQAAAAAAAAAGPGQQGPGQ

QGPGEQGPGSGGPGQQAAAAAAAAAGPGQQGPGQQGPGEQGPGSGSGPG

QIYYGPQSVAAPAAAAASALAAPATSARISSHASALLSNGPTNPASISNV

ISNAVSQISSSNPGASACDVLVQALLELVTALLTIIGSSNIGSVNYDSSG

QYAQWTQSVQNAFA

The A10 4mer BWT protein was readily produced and purified from the SoluBL21-pLysS strain at 96 (±12) mg/L.

Figure 9:
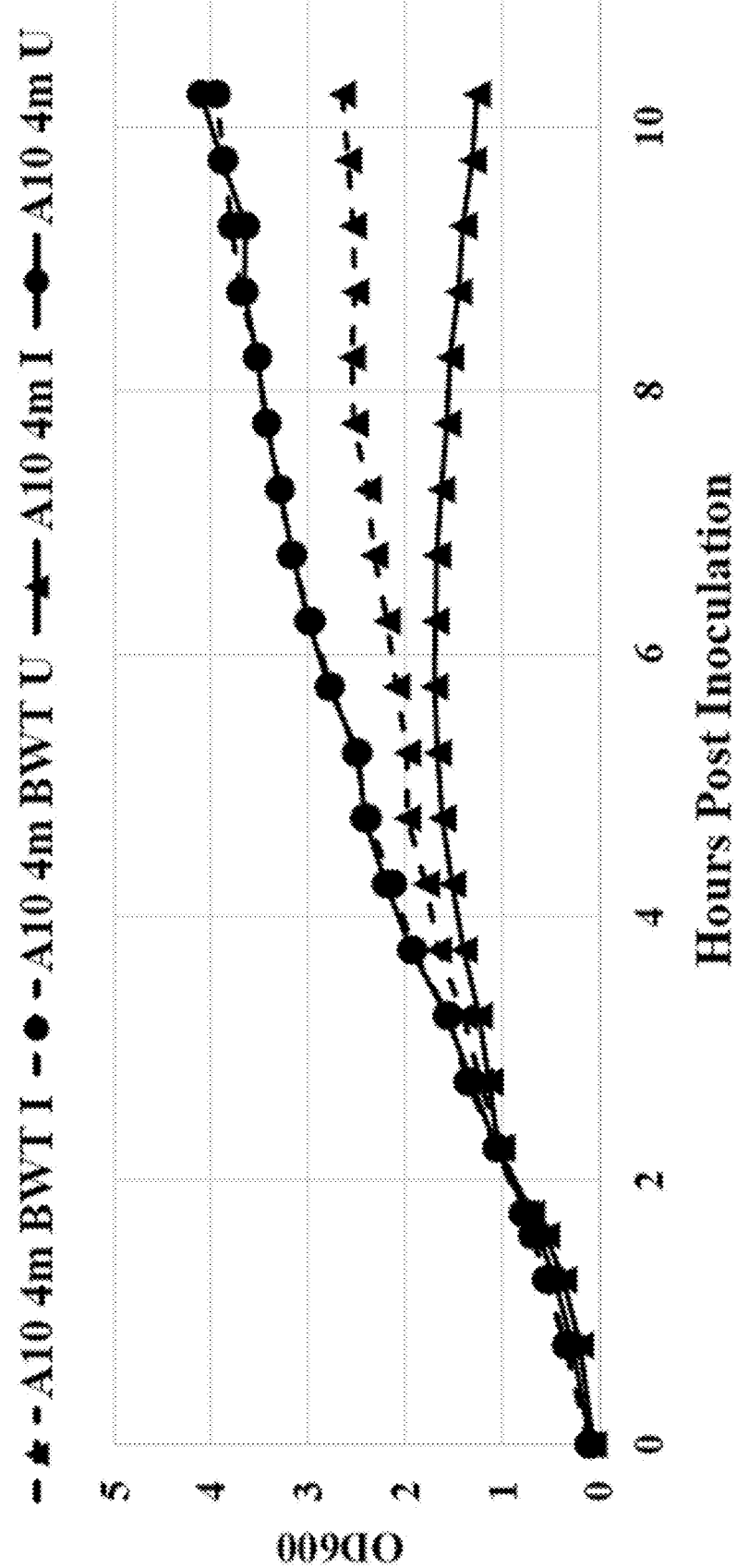
FIG. 9 is a graph showing cell growth during expression of the A10 4mer and A10 4mer BWT constructs with and without induction.
Figure 10:
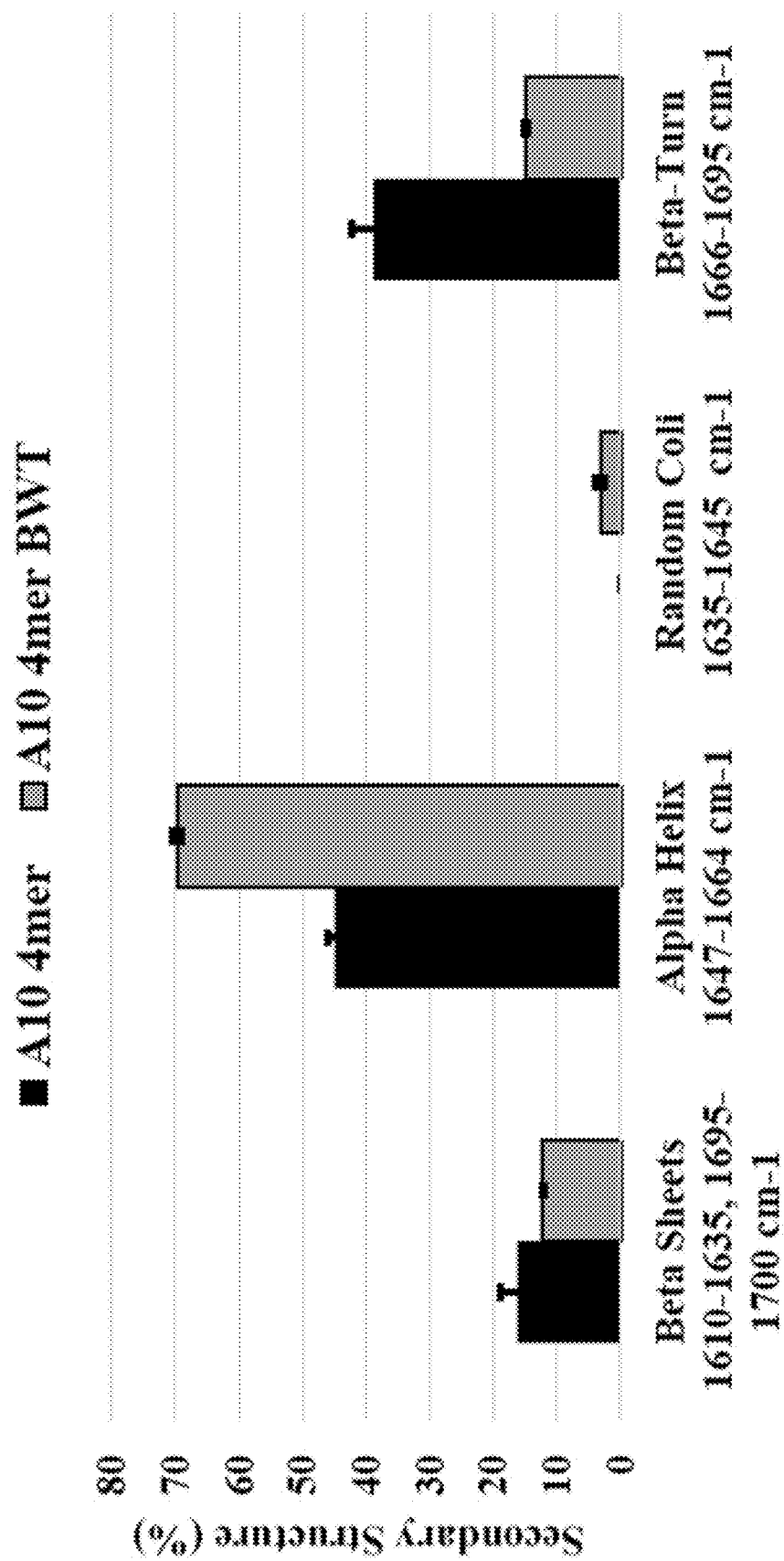
FIG. 10 is a graph showing the secondary structure of A10 4mer and A10 4mer BWT constructs as determined by Fourier-transform infrared spectroscopy (FTIR)
Figure 11:
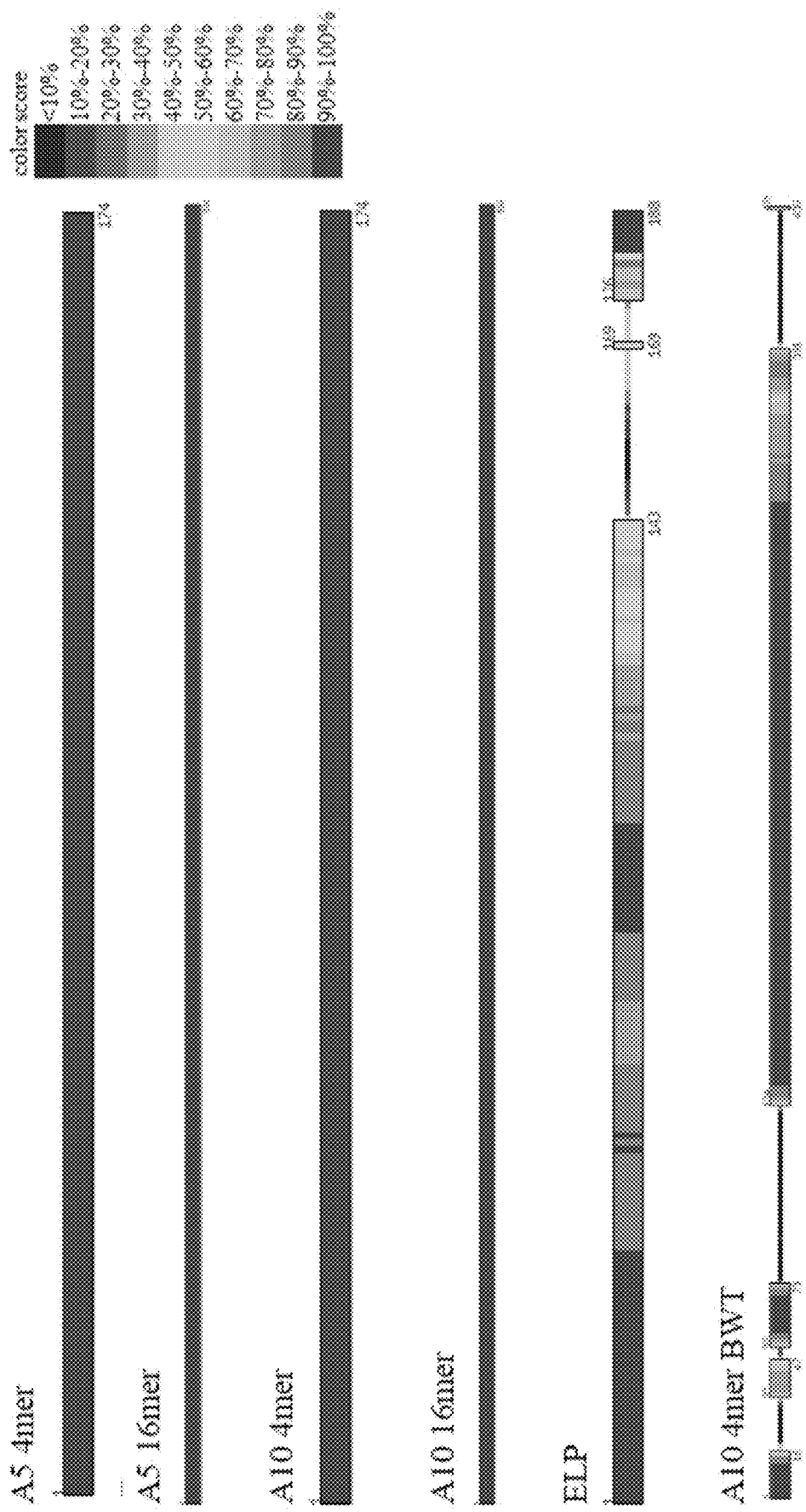
FIG. 11 is an image showing DisMeta/DISOPRED3 computational disorder predictions for recombinant spidroins and ELP.

FIG. 9 shows the growth of strain SoluBL21-pLysS over 10.25 hours during induced expression of the A10 4mer and A10 4mer BWT constructs, with uninduced cultures serving as controls. Including the black widow termini increases the final OD600 versus the original A10 4mer by 110%. Unlike the original A10 4mer expressions, during expression of A10 4mer BWT, the strain exhibits a later stationary phase, and no death phase is observed over the 10.25 hours. Fourier-transform infrared spectroscopy (FTIR) data on the constructs shows that there is a substantial shift in protein structure when the terminal domains are included, with A10 4mer BWT demonstrating an increase in alpha helices and a decrease in beta turns (see FIG. 10). Decreased disorder of A10 4mer BWT versus A10 4mer is supported by observation of more normal mobility in SDS PAGE, where the 43 kDa A10 4mer BWT shows an apparent molecular weight of 48 kDa while the 15 kDa A10 4mer shows an apparent weight of 27 kDa. Furthermore, computational disorder predictions for the A10 4mer BWT show large regions where individual residues have less than 10% probability of disorder, while the original A10 4mer construct is shown to have 90-100% probability of disorder at all residues (see FIG. 11). Embodiments of the present disclosure utilizing terminal domains are particularly advantageous to mitigate toxicity where a toxic recombinant protein sequence cannot be altered due to requirements of a specific application. In some embodiments, the flanking terminal domain sequences can then be subsequently removed through the inclusion of cleavage sequences.

Methods and systems of the present disclosure advantageously leverage recombinant *E. coli* strains and synthetic protein designs for production of disordered polypeptides such as spidroins and ELPs. Downregulation of basal expression in the recombinant bacteria of the present disclosure result in high titers of disordered protein product while minimizing the toxic effects thereof, enabling the economical production of these desired polypeptide constructs at industrially-relevant scales. Examples of functionalities related to the improved titers for the *E. coli* platform include an increased potential for next-generation biopolymers to function as enhanced replacements for current materials by way of improved unit economics. Examples of functionalities related to the production of recombinant spidroins and ELPs include tissue regeneration, sustainable clothing and textiles, drug delivery, food preservation, and biomedical implants. These methods can also be applied to different permutations of de novo designed recombinant spidroin or elastin-like peptides, as well as other protein-based biopolymers of interest, such as collagen, that share similarities in primary sequence composition, aggregation propensity, and intrinsic disorder.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A recombinant bacteria for producing polypeptides, comprising:
an E. coli strain, wherein the E. coli strain includes:
one or more exogenous nucleotide sequences encoding a disordered polypeptide, the disordered peptide including a primary sequence selected from the group consisting of:
(a) GPGQQ AAAAA GPGQQ GPGQQ GPGQQ GPGEQ GPGSG (SEQ. ID NO.: 1),
(b) GPGQQ AAAAA AAAAA GPGQQ GPGQQ GPGEQ GPGSG (SEQ. ID NO.: 2),
(c) (VPGAGVPGAGVPGAGVPGAGVPGYGVP-GAGVPGAGVPGAGVPGAG VPGYG)₂ GRGDS (SEQ. ID NO.: 3), and
(d) combinations thereof;
one or more mutations to stress-response genes from wild-type E. coli B; and
at least one promoter regulating the expression, in the E. coli strain, of the one or more exogenous nucleotide sequences;
wherein basal expression of the one or more exogenous nucleotide sequences is inhibited such that incubation in an about 0.6 to about 0.8 OD600 culture of the E. coli strain for about 4 hours produces less than about 7 mg/L disordered polypeptide in the culture.

2. The recombinant bacteria according to claim 1, wherein the E. coli strain includes a SoluBL21 genome and a pLysS plasmid.

3. The recombinant bacteria according to claim 1, wherein the E. coli strain includes one or more mutations in at least one of the following genes:
yggw, yedv, yedw, yedy, spec, speb, uspc, hcha, loip, mltc, envz, ompr, yhgf, and hupb.

4. The recombinant bacteria according to claim 1, wherein the disordered polypeptide includes:
between about 30% and about 40% glycine residues; and
between about 10% and about 20% proline residues.

5. The recombinant bacteria according to claim 1, wherein the disordered polypeptide includes recombinant spidroins, elastin-like peptides (ELPs), or combinations thereof.

6. The recombinant bacteria according to claim 1, wherein the at least one promoter regulating the expression of the one or more exogenous nucleotide sequences includes a T7 polymerase promoter, and wherein the basal expression of the one or more exogenous nucleotide sequences is inhibited via production by the *E. coli* strain of T7 lysozyme.

* * * * *